United States Patent [19]

Vassbotn et al.

[11] Patent Number: 5,444,151

[45] Date of Patent: Aug. 22, 1995

[54] PLATELET DERIVED GROWTH FACTOR ANTAGONISTS

[75] Inventors: Flemming S. Vassbotn; Maria Andersson; Gudrun Backstrom; Ulla Engström; Carl-Henrik Heldin; Ulf Hellman; Arne Ostman; Bengt Westermark, all of Uppsala, Sweden

[73] Assignee: Ludwig Institute for Cancer Research, New York, N.Y.

[21] Appl. No.: 977,234

[22] Filed: Nov. 16, 1992

Related U.S. Application Data

[63] Continuation-in-part of Ser. No. 883,949, May 15, 1992, Pat. No. 5,326,695.

[51] Int. Cl.⁶ .................. C07K 13/00; C07K 7/00; C07K 99/00
[52] U.S. Cl. .................. 530/324; 530/325; 530/326; 530/327; 530/399; 530/402; 530/408; 530/350; 930/120
[58] Field of Search .......... 530/350, 399, 324, 325, 530/326, 327, 402, 408

[56] References Cited

U.S. PATENT DOCUMENTS

| | | | |
|---|---|---|---|
| 4,845,075 | 7/1989 | Murray et al. | 514/12 |
| 4,889,919 | 12/1989 | Murray et al. | 530/351 |
| 5,128,321 | 7/1992 | Murray et al. | 514/12 |
| 5,132,408 | 7/1992 | Baird et al. | 530/399 |
| 5,149,691 | 9/1992 | Rutherford | 514/12 |

FOREIGN PATENT DOCUMENTS

0288307 11/1990 European Pat. Off. .
WO9014425 2/1988 WIPO .

OTHER PUBLICATIONS

Heldin et al., Cell Reg. 1: 555–566 (Jul. 1990).
Ostman et al., J. Biol. Chem. 263: 16202–16208 (1988).
Truett et al., DNA 4(5):333–349 (1985).
Betsholtz, C. et al., Nature, 320: 695–699, 1986.
Ostman, A. et al., J. Biol. Chem., 266(16): 10073–10077, 1991.
LaRochelle, W. et al., Science, 248: 1541–1544, 1990.

Primary Examiner—Garnette D. Draper
Assistant Examiner—Marianne Allen
Attorney, Agent, or Firm—Felfe & Lynch

[57] ABSTRACT

The invention describes antagonists for PDGF. The antagonists contain amino acids, and may be monomers or dimers. Especially preferred are dimers which bind the PDGF receptors, but prevent dimerization of the bound receptors. Dimerization is necessary for PDGF effect, hence the antagonistic effect. Also described are nucleic acid sequences for making the antagonists, as well as cell lines transfected with the material.

5 Claims, 23 Drawing Sheets

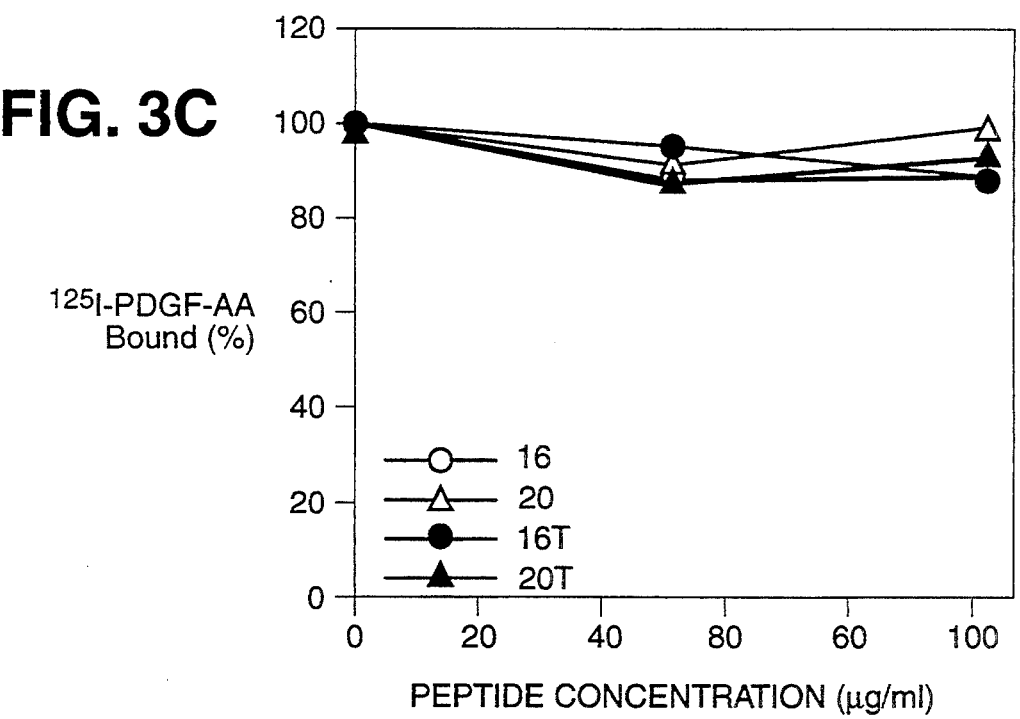
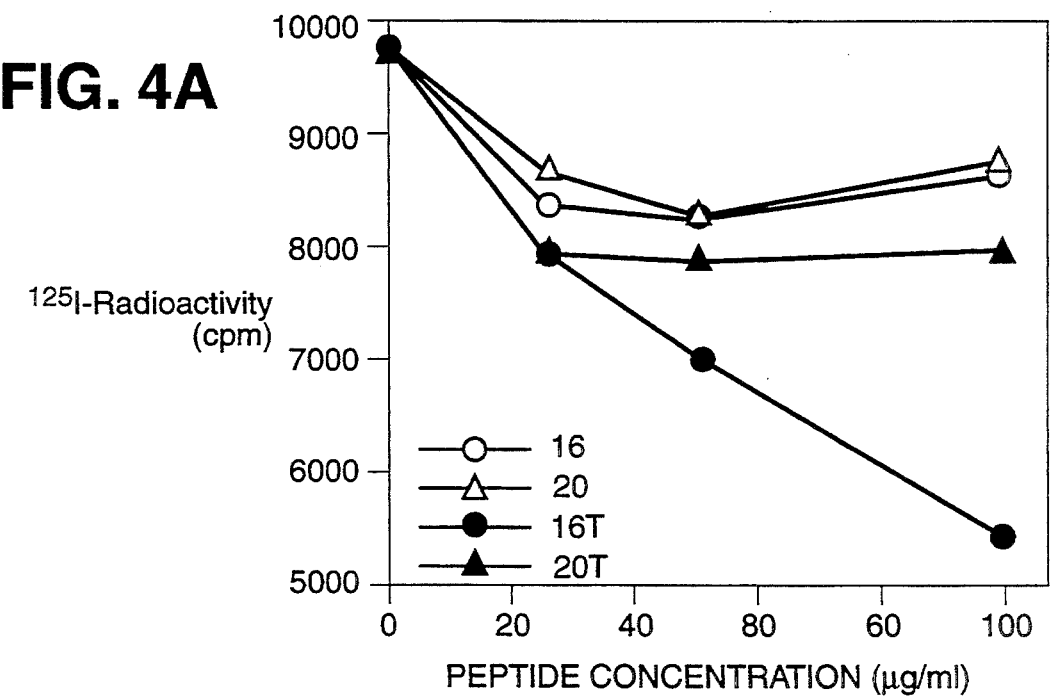

FIG. 8A
FIG. 8B
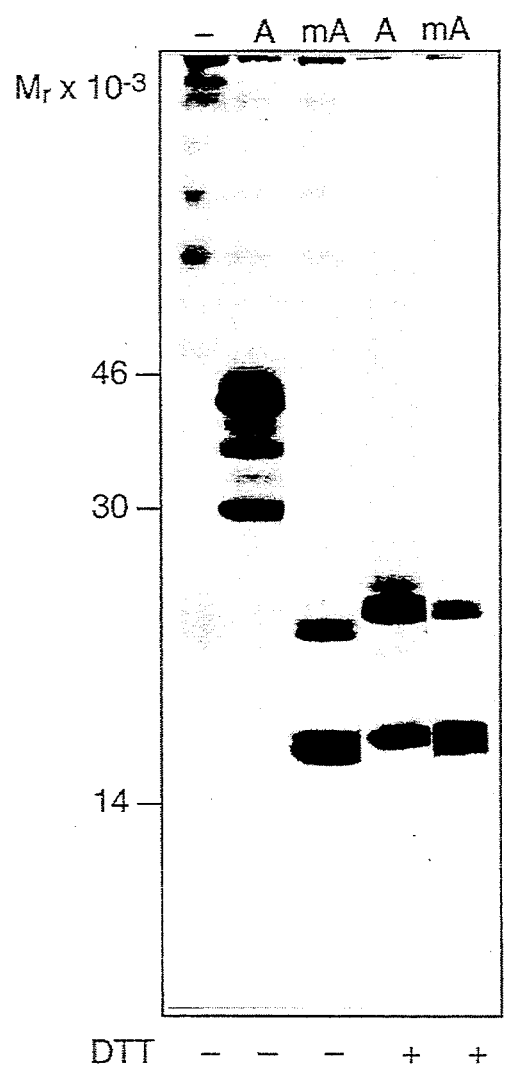
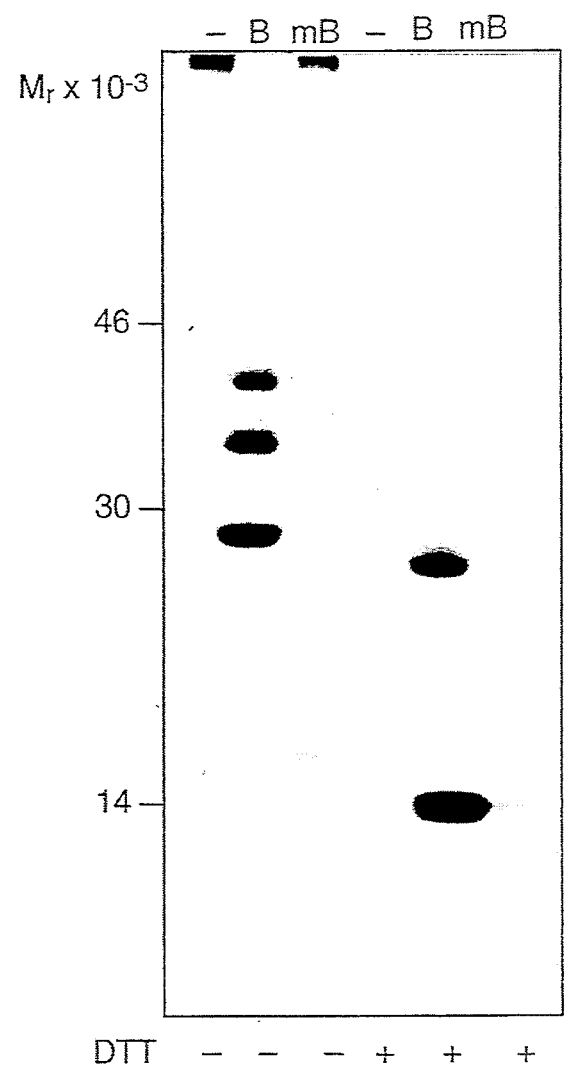

PLATELET DERIVED GROWTH FACTOR ANTAGONISTS

This application is a continuation-in-part of U.S. patent application Ser. No. 883,949 filed on May 15, 1992, now U.S. Pat. No. 5,326,695.

FIELD OF THE INVENTION

This invention relates to antagonists of the molecule known as platelet derived growth factor, or "PDGF". More particularly, it refers to amino acid containing antagonists, both monomers and dimers, for PDGF-BB. Also described are various nucleic acid based materials useful in preparing the antagonists, as well as uses therefor.

BACKGROUND AND PRIOR ART

PDGF was first recognized as a component of platelet α granules, which had growth promoting activity for smooth muscle cells and fibroblasts (Heldin and Westermark, Cell Regul 1: 555–566 (June 1990)). It has also been implicated in the stimulation of connective tissue—derived cells in vitro (Östman et al., J. Biol. Chem. 263(31): 16202–16208 (November 1988)), as the major mitogenic protein for mesenchymal cells (Murray et al., U.S. Pat. Nos. 4,889,919 and 4,845,075), and as an inducer of cell multiplication and DNA synthesis in cultured muscle cells, fibroblasts and glial cells (Kelly et al, PCT Application WO90/14425 (Nov. 29, 1990)). It has also been shown to be involved in the wound healing response (Ross et al., N. Eng. J. Med. 295:369 (1976)), and may be involved in a causative role for the development of proliferative lesions of atherosclerosis (Ross) supra. Others have suggested that this molecule may be a mediator of tumor development as well as in nonmalignant proliferative disorders (Heldin et al., supra).

The PDGF molecule has been very well characterized. It is known to exist as a heterodimer of an "A" chain and a "B" chain, connected to each other via disulphide bonds. The dimer, sometimes referred to as "PDGF-AB", has a molecular mass of about 30 KDa. Amino acid sequences are known for both the A and B chains, as shown, e.g., by Murray et al., U.S. Pat. Nos. 4,889,919 and 4,845,075, the disclosures of which are incorporated by reference. The mature chains contain slightly more than 100 amino acids, and are about 60% homologous. Heldin et al., supra.

Dimers PDGF-AA and PDGF-BB have been produced via recombinant means, and have also been isolated from natural sources (see Murray et al., Supra; Heldin et al., Supra). The various dimers, or "isoforms" differ in functional properties and secretory behavior.

The mechanism by which PDGF acts on cells has received intensive scrutiny, and it has been established that there are two receptors for PDGF, the "α" and "β" receptors. The α receptor binds all isoforms, whereas the β receptor does not bind PDGF-AA, binds PDGF-AB with low affinity, and PDGF-BB with high affinity (Heldin et al., supra; Ö stman et al., supra). The α receptor is synthesized as a 140 KDa precursor protein which matures to one of 170 KDa, and the β receptor is recognized as a precursor of 160 KDa, and a mature molecule of 180 KDa. cDNA for both receptors have also been isolated (Heldin et al., supra; Kelly et al., supra).

The receptors both comprise five immunoglobulin like domains (extracellular portion), and intracellular portions containing protein tyrosine kinase domains with characteristic insert sequences which have no homology to kinase domains (Yarden et al., Nature 323: 226–232 (1986); Matsui et al., Science 243: 800–803 (1989)); Claesson-Welsh et al., PNAS 86: 4917–4921 (1989). When PDGF binds to these receptors, dimerization of the receptor molecules is induced, followed by kinase activation and autophosphorylation of the receptors (Heldin et al., J. Biol. Chem. 264: 8905–8912 (1989); Seifert et al., J. Biol. Chem. 264: 8771–8778 (1989); Bishayee et al., J. Biol. Chem. 264: 11699–11705 (1989)).

The diverse actions of PDGF and its suggested involvement in disease states would indicate that the use of agonists and antagonists may be useful in defining the action of PDGF and of alleviating some of the disorders. These molecules, using the definitions employed by Kelly et al., supra, either mimic the effect of PDGF (agonists), or block the interaction of receptor and ligand (antagonists).

The art has long recognized that agonists and antagonists for various materials exist, and Kelly et al., via their discussion, de facto assume that these exist for PDGF. Review of the literature indicates, however, that no proteinaceous agonists and antagonists to PDGF are taught. For the reasons described supra, it would be desirable to have such material available.

The two patents to Murray et al., cited supra discuss potential amino acid substitution of cysteine residues in the monomeric chains, provided that these substitutions do not destroy the biological activity of the molecules. The '919 patent generally teaches modifications of PDGF AA molecules. Neither reference teaches that modified dimers of PDGF have antagonistic activity against wild type PDGF.

It has now been found that substitutions within the amino acid chain of PDGF monomers leads to the production of antagonists to PDGF-BB. As PDGF-BB is implicated in the transformation of cells, the antagonists have value in a therapeutic context, as well as in various other milieux, as described in the disclosure which follows.

BRIEF DESCRIPTION OF THE FIGURES

FIGS. 3A, 3B and 3C depicts competitive activity of various HPLC purified PDGF derived peptides on binding of various ligands to PDGF receptors.

FIGS. 4A, 4B and 4C present data showing the inhibiting effect of various PDGF derived peptides on $^{125}$I-labeled PGF-AA internalization and degradation.

FIG. 7B sets forth amino acid sequences for the peptides eluted from the HPLC experiments of FIG. 7A.

The amino acid sequence, i.e., the top line, is set forth in SEQ ID NO: 7.

FIGS. 8A and 8B show analysis of immunoprecipitated, conditioned medium following labelling with [$^{35}$S]-cysteine.

Figure 9:
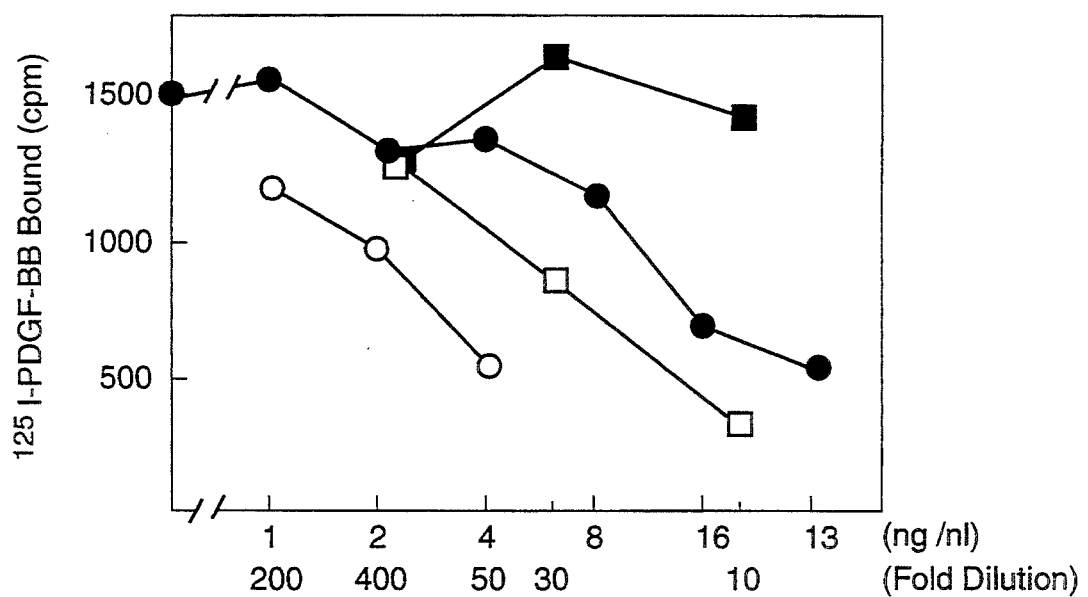

FIG. 9 shows experiments involving cell growth and competition between $^{125}$-PDGF-BB and serial dilutions of peptides.

Figure 10B:
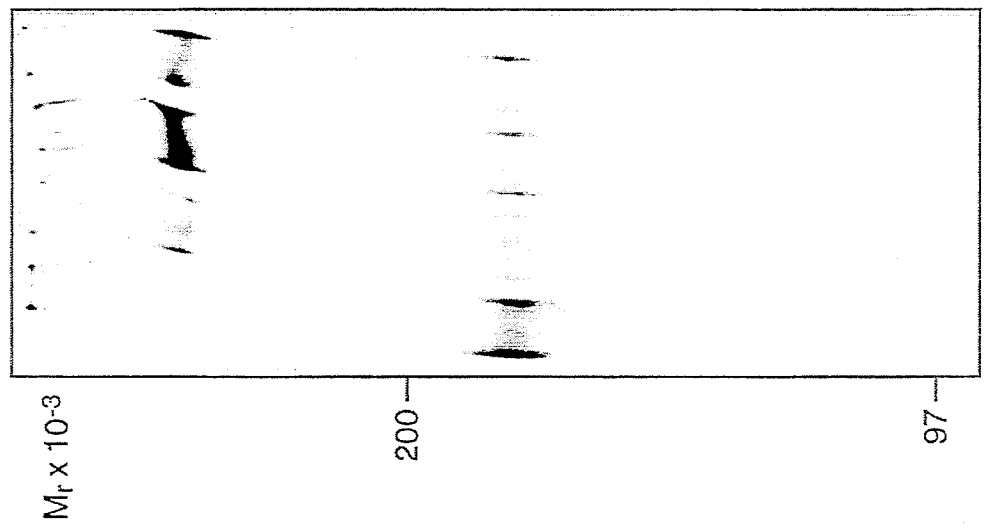
Figure 10A:
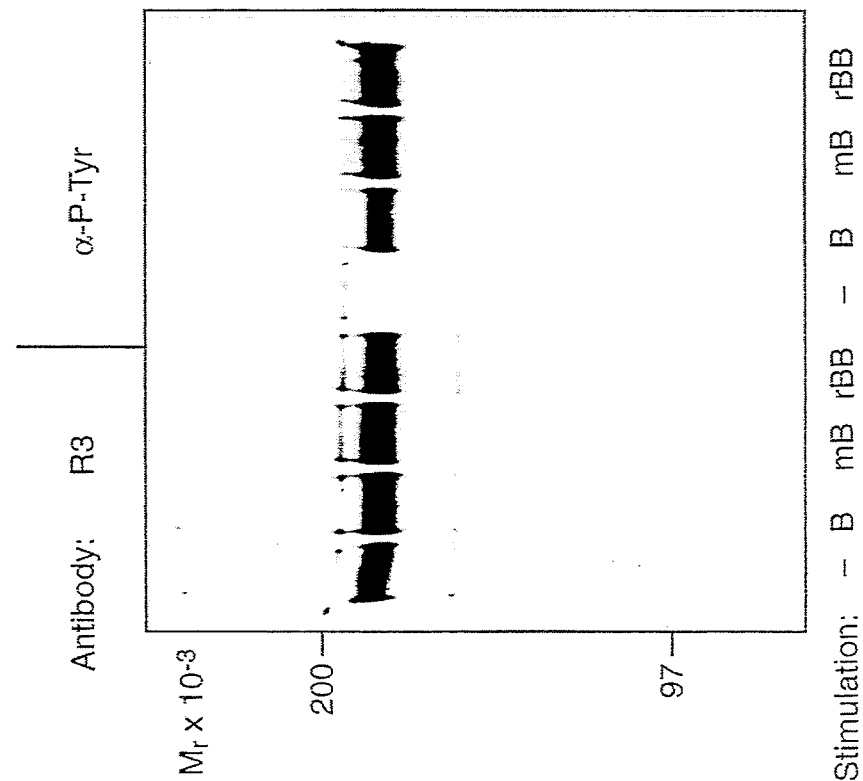

FIGS. 10A and 10B show SDS-PAGE immunoprecipitation studies using PDGF B derivatives (10A) and the effect of derivatives on dimerization (10B).

Figure 11A:
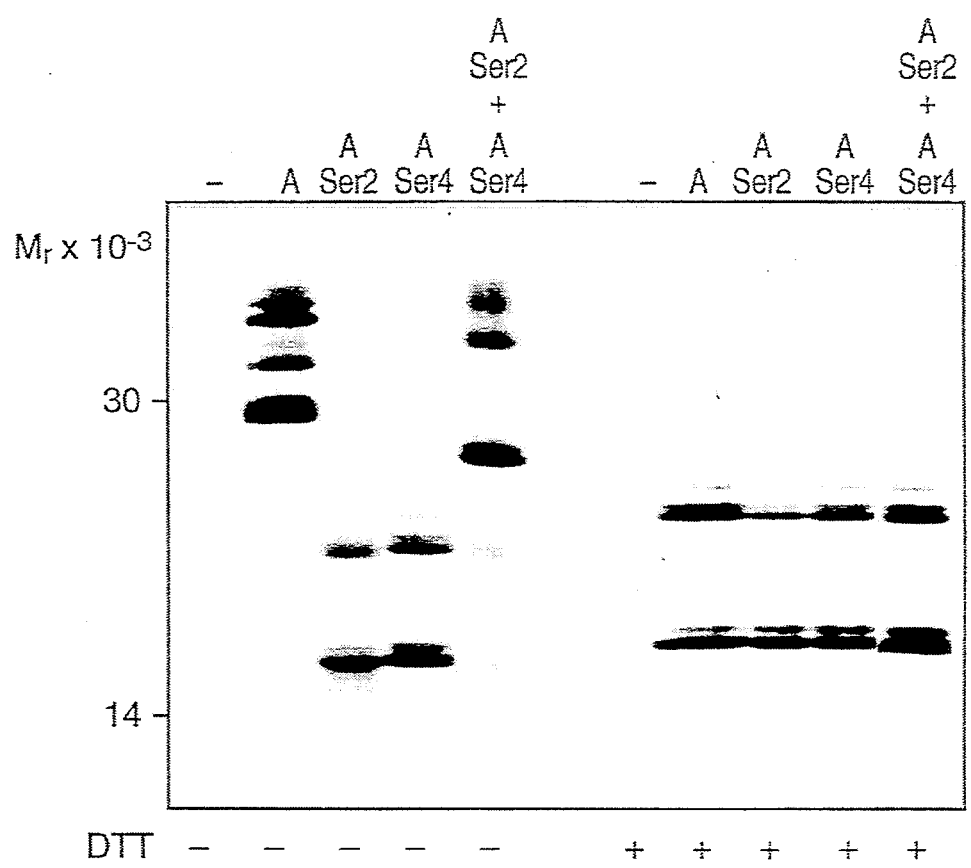

FIG. 11A shows studies on PDGF-AA dimer formation.

Figure 11B:
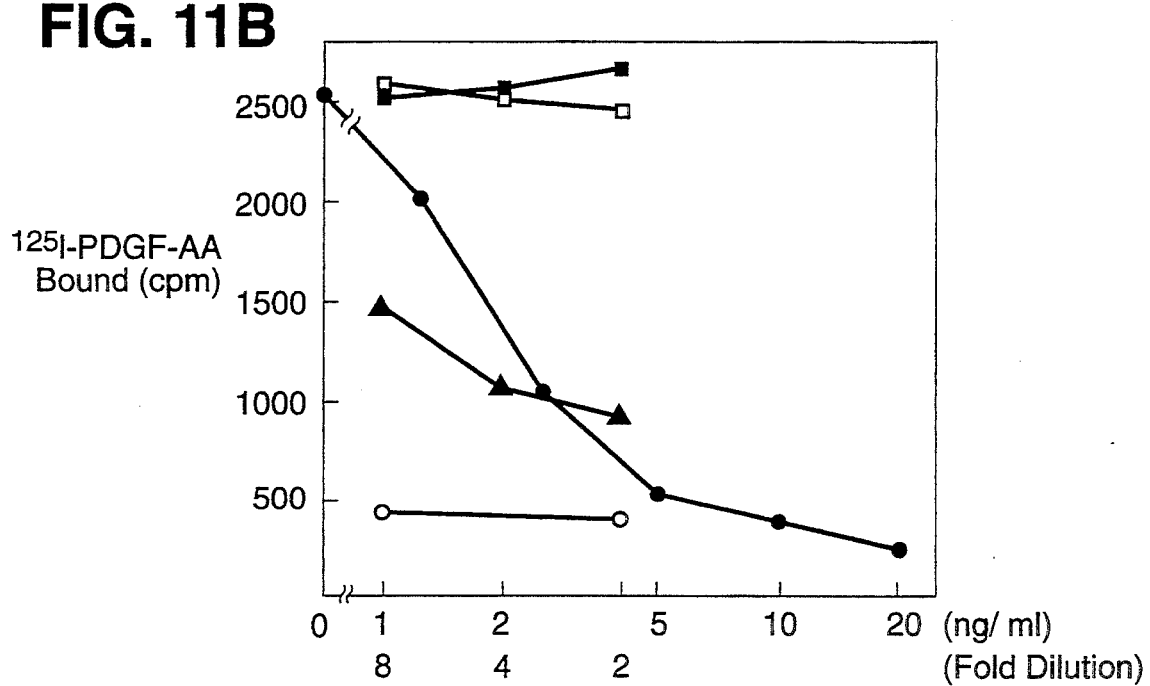

FIG. 11B shows receptor competing activity of single bonded dimers.

Figure 12:
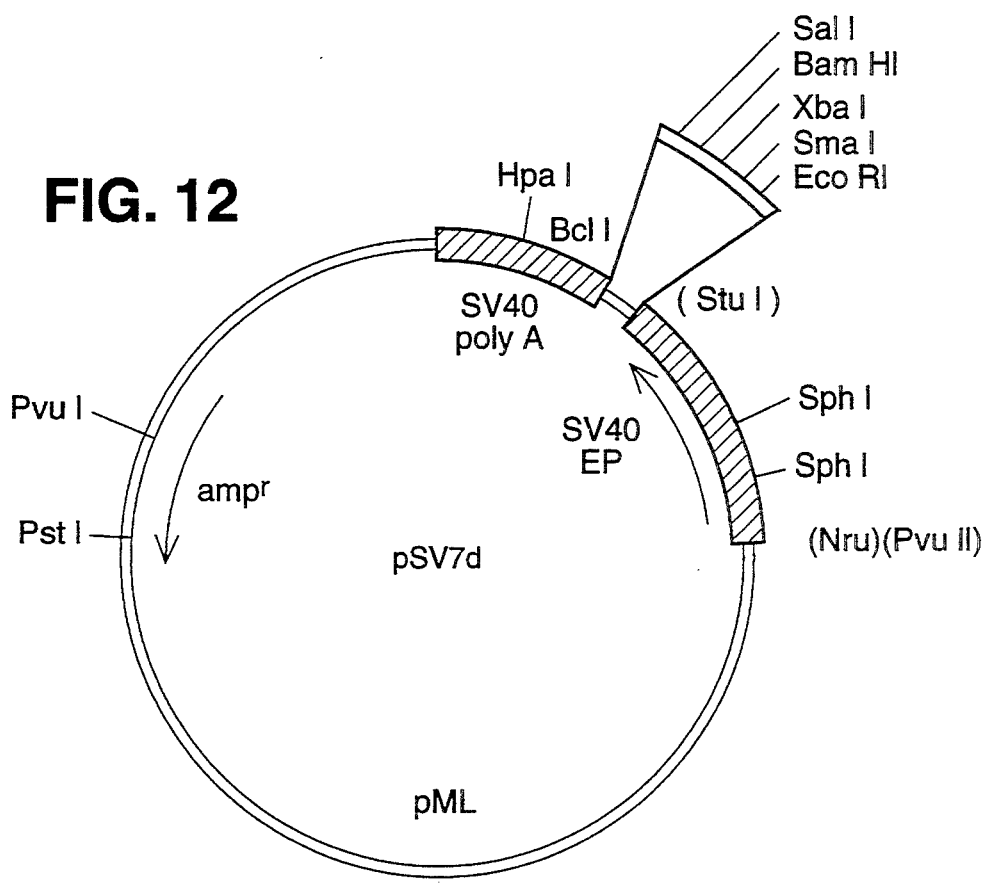

FIG. 12, labelled PRIOR ART, is the restriction map of plasmid pSV7d.

Figure 13:
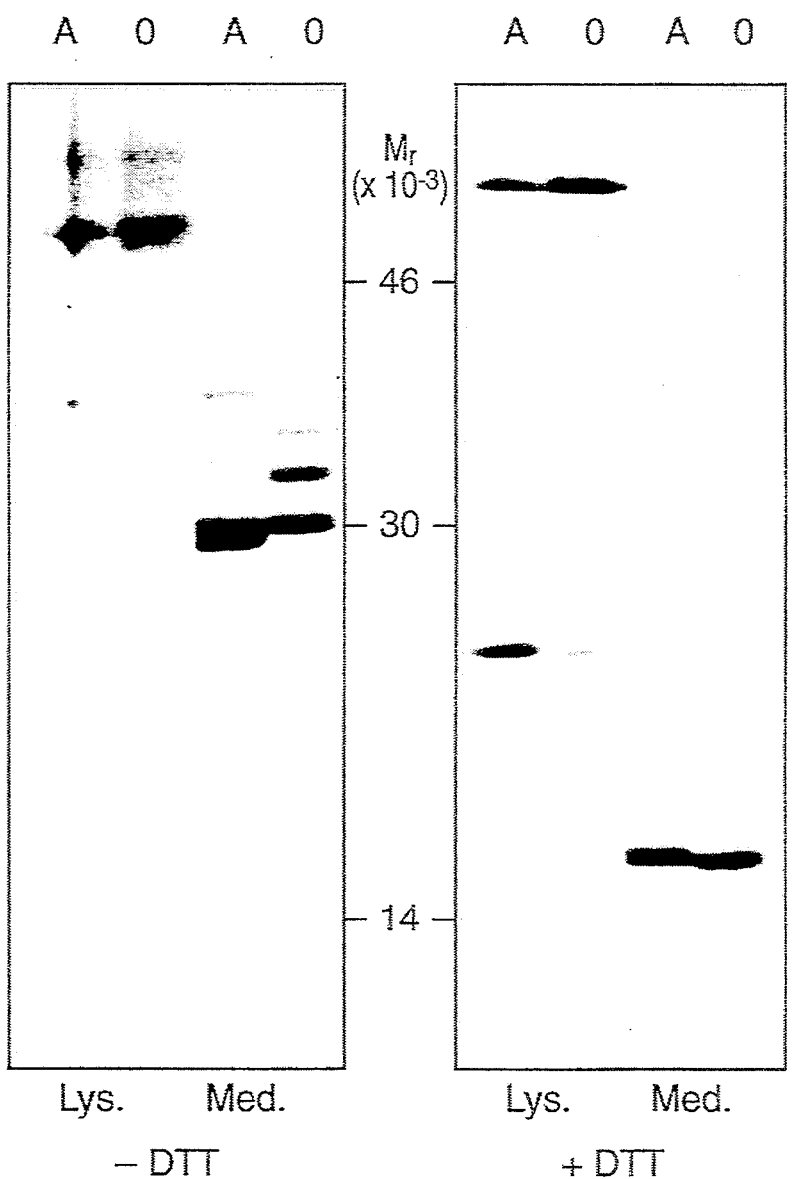

FIG. 13 generally shows the immunoprecipitation of PDGF-A and the mutant PDGF-O following expression in COS cells.

Figure 14:
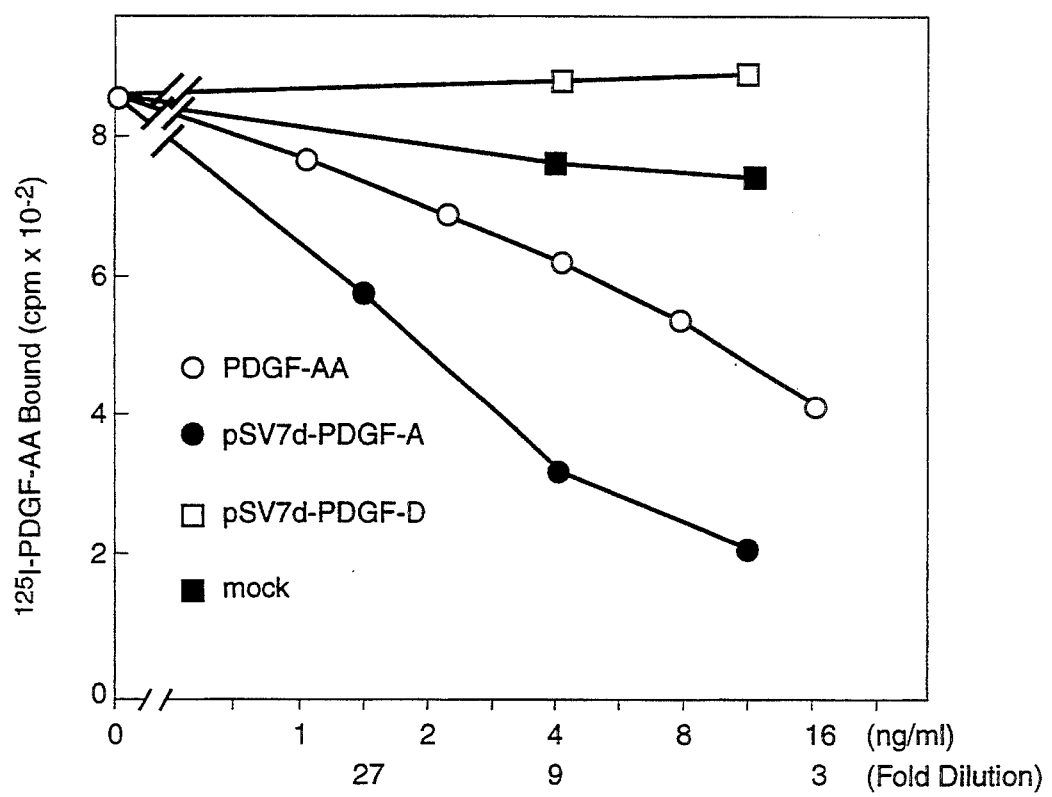

FIG. 14 depicts the results of binding assays using the mutant PDGF-O and PDGF-A.

Figure 15B:
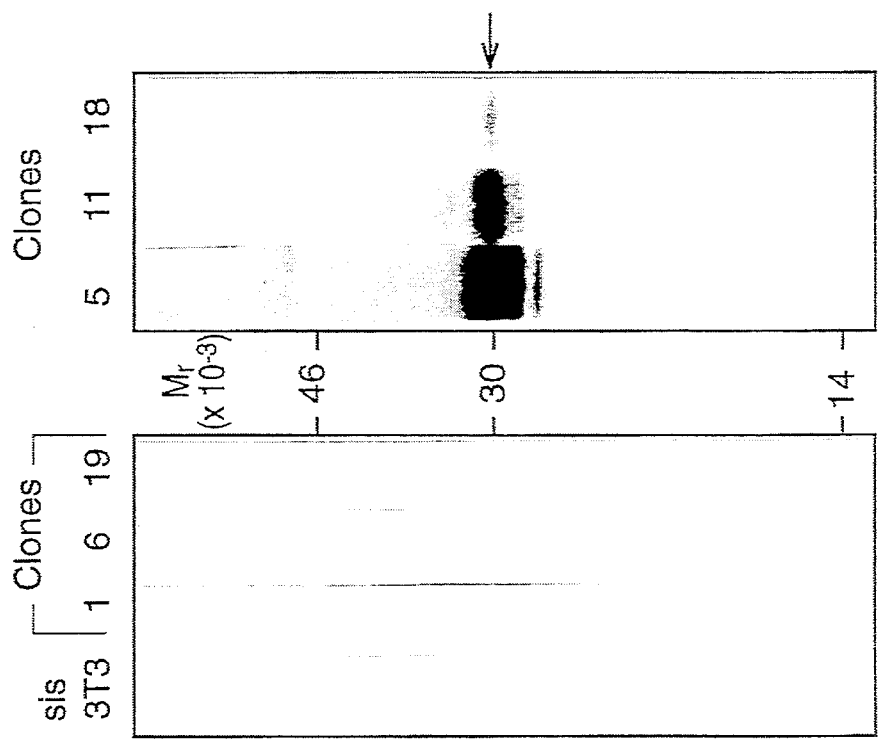
Figure 15A:
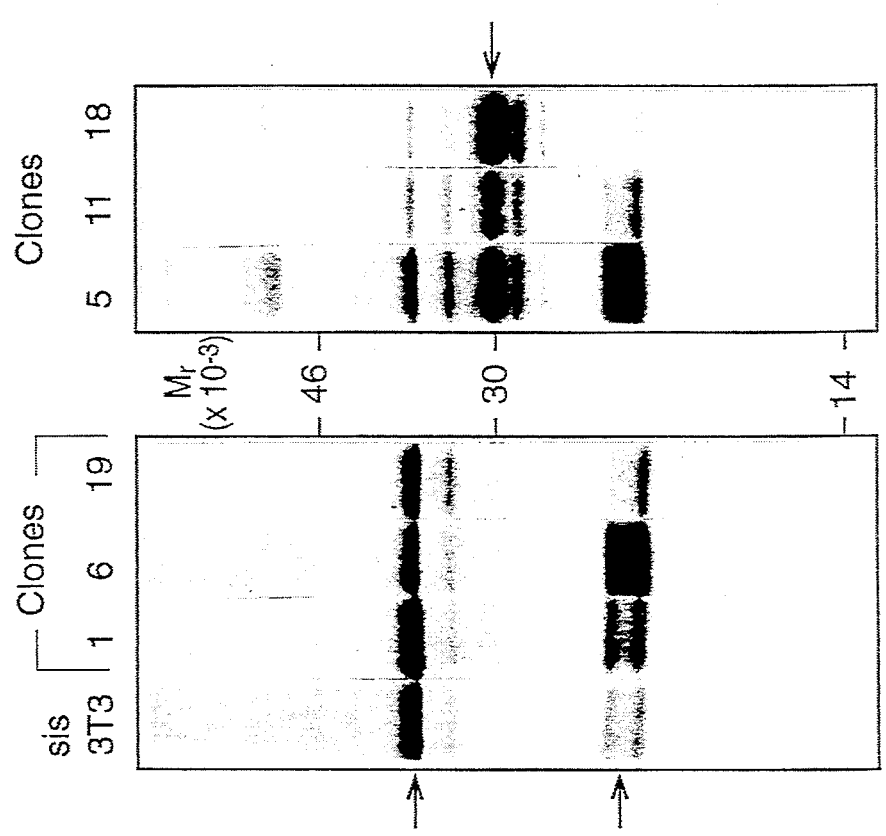

FIGS. 15A and 15B presents data concerning the immunoprecipitation of PDGF-B producing cells following transfection with PDGF-O DNA.

Figure 16:
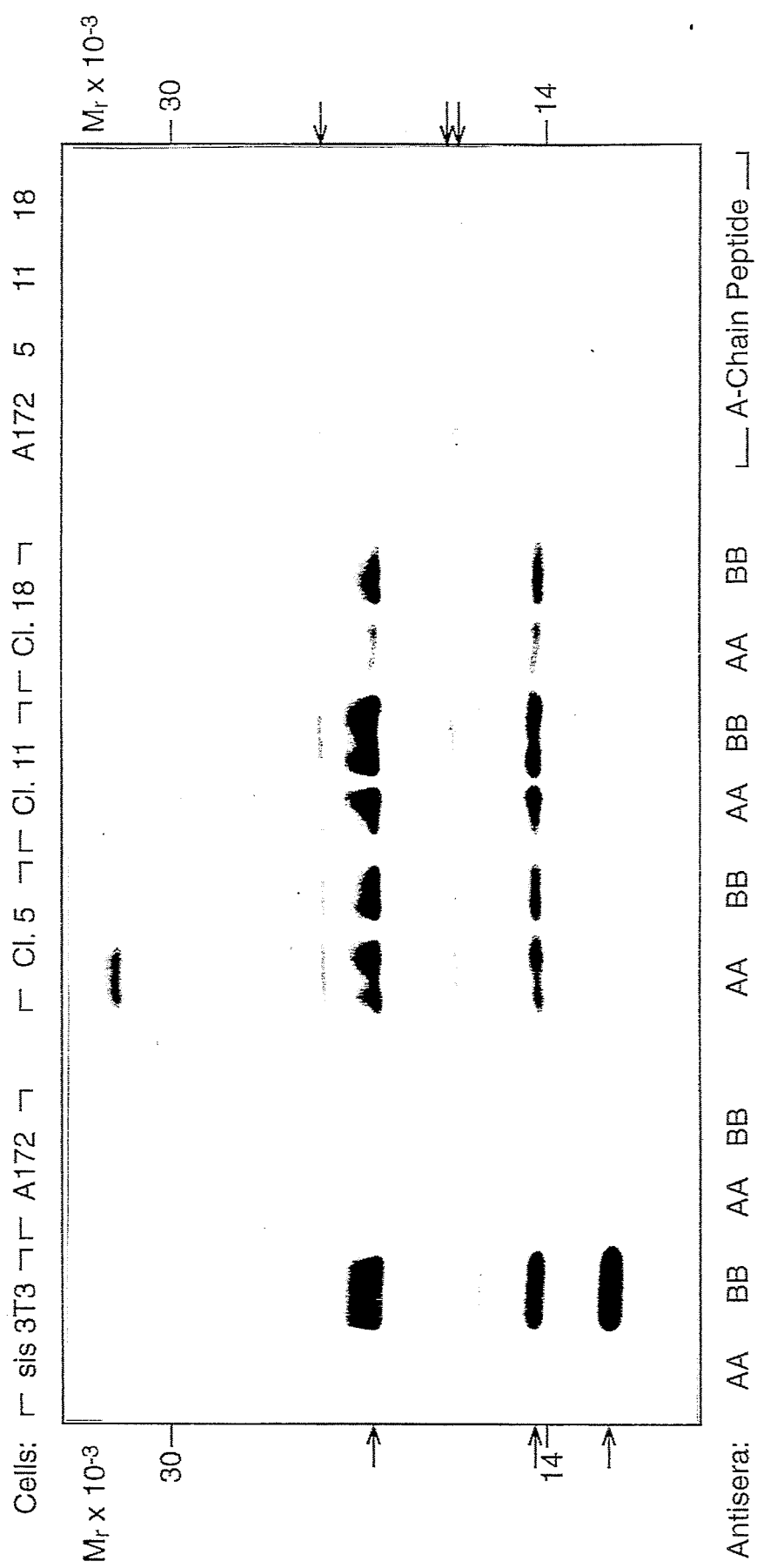
Figure 17A:
Figure 17B:
Figure 17C:
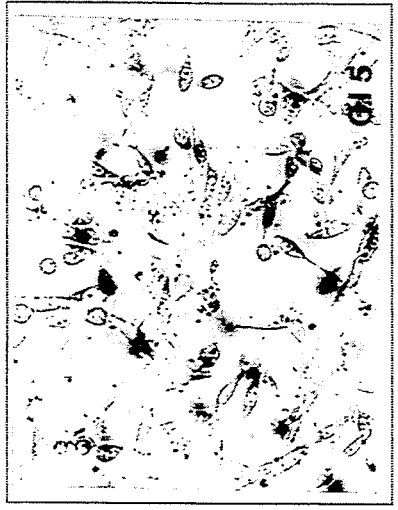
Figure 17D:
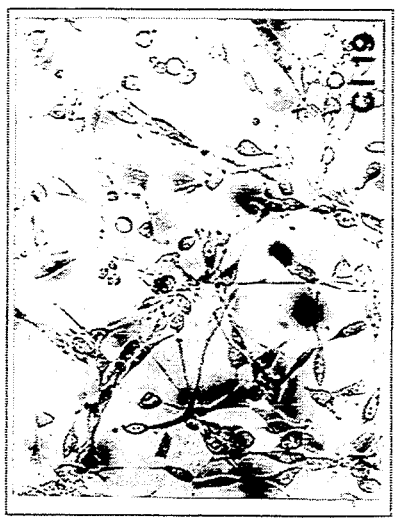
Figure 17E:
Figure 17F:
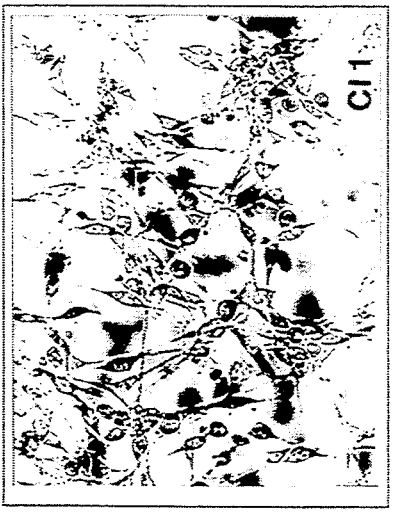

FIG. 16 shows the production of PDGF-OB heterodimers by pSV7d-PDGF-O transfected sis3T3 cells.

FIGS. 17A–17F, inclusive compare the morphology of sis3T3 PDGF-O producers to non producers.

Figure 18:
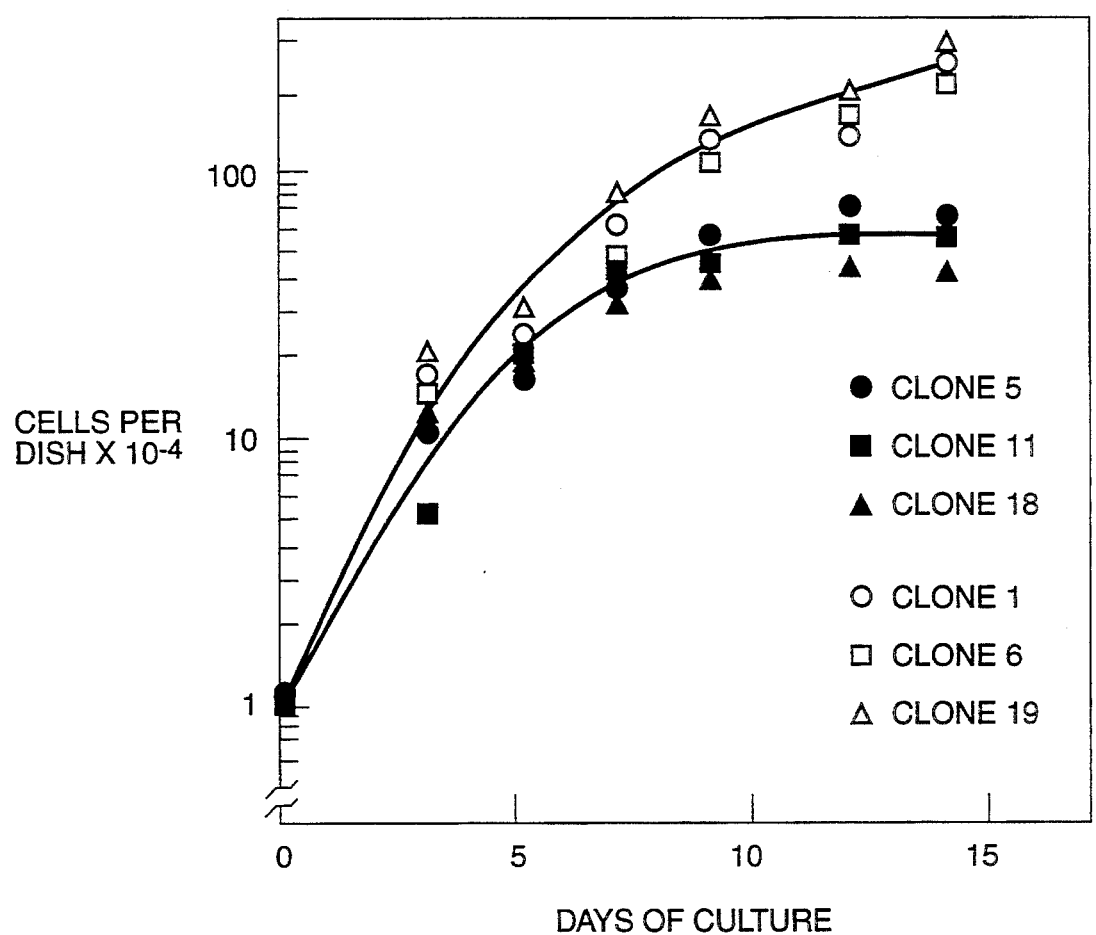
Figure 19C:
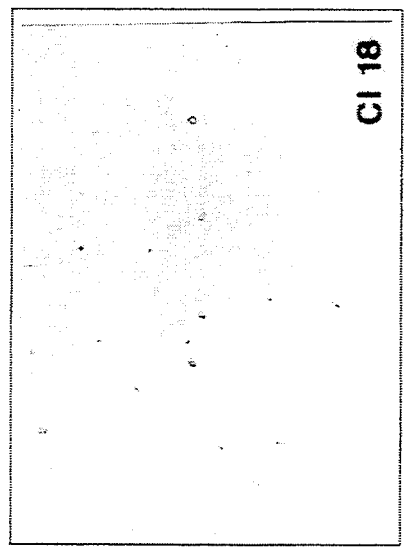
Figure 19B:
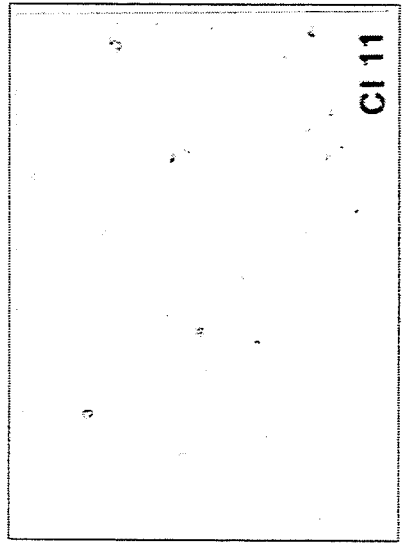
Figure 19A:
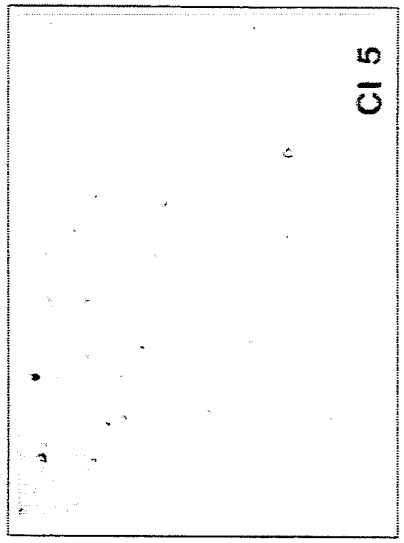
Figure 19F:
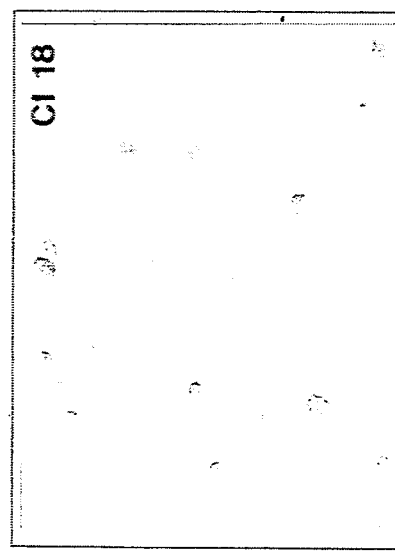
Figure 19E:
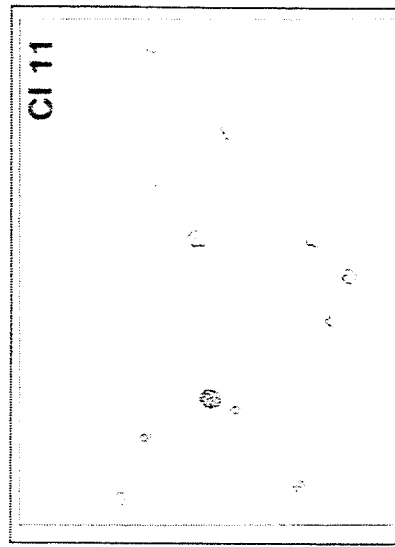
Figure 19D:
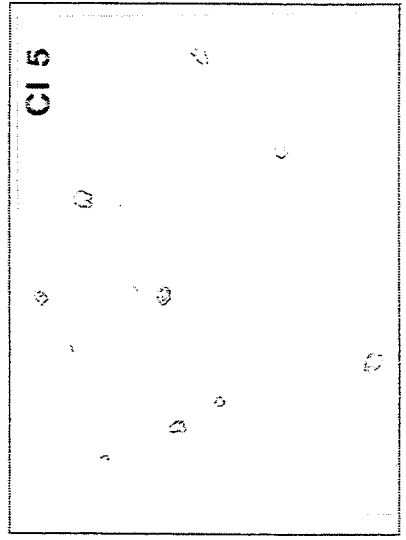
Figure 19I:
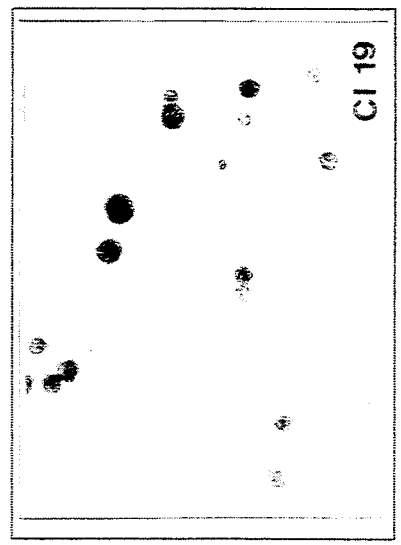
Figure 19H:
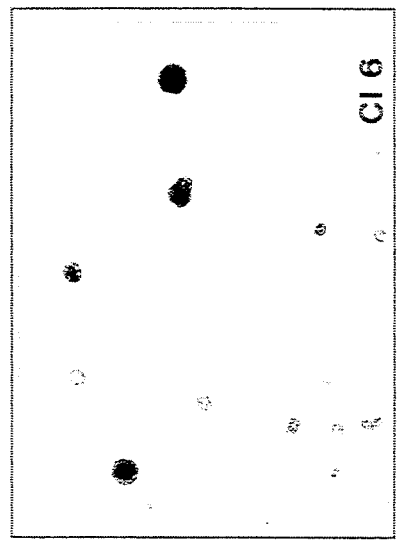
Figure 19G:
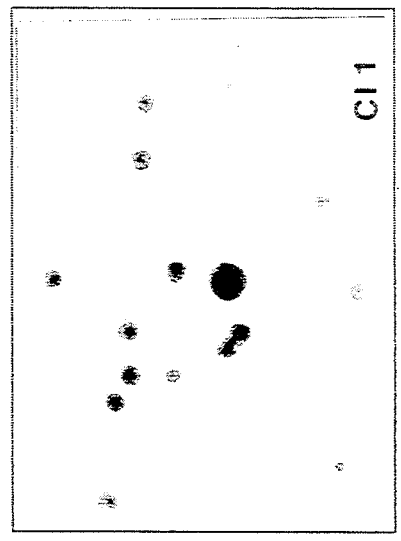

FIG. 18 presents, in graph form, data regarding the effect of PDGF-O on sis3T3 proliferation.

FIGS. 19A–19I, inclusive, show the effect of PDGF-O on colony formation of sis3T3 cells.

DETAILED DESCRIPTION OF PREFERRED EMBODIMENTS

Example 1

In order to test for receptor binding, cultures of human foreskin fibroblast cell line AG1518 (obtained from the Human Mutant Cell Repository), were grown to confluence in Ham's F-12 medium containing 10% newborn calf serum. Those cells which were to be used in analysis of PDGF-β receptor binding were preincubated for 60 minutes at 37° C. in 0.5 ml/well of Ham's F-12 medium, supplemented with 1 mg/ml of bovine serum albumin (BSA), and 50 ng/ml of PDGF-AA. This combination down regulates PDGF-α receptor, as per Claesson-Welsh et al., J. Biol. Chem. 264: 1742–1747 (1989).

Cells were prepared for receptor binding analyses by washing with ice cold binding buffer (phosphate buffered saline with 0.9 mM CaCl$_2$, 0.49 mM MgSO$_4$ and 1 mg/ml BSA). The cells were then incubated on ice for 90 minutes with different concentrations (0–100 ug/ml) of synthetic peptides (listed in Table 1, infra), in 0.5 ml of binding buffer per well. This was followed by addition of $^{125}$I labelled PDGF-AA, PDGF-BB, or EGF. The labelled ligand was added and then incubated for 60 minutes at 0° C. after which the cells were washed five times with ice cold binding buffer. The washed cells were then lysed for 60 minutes at room temperature in a lysis buffer (1% Triton X-100, 10% glycerol, 20 mM Tris-HCl, pH 7.5). Solubilized radioactivity was determined in a gamma counter. Competing activities of synthetic peptides were compared to standard curves, using unlabelled ligand.

The peptides used were all derived from the amino acid sequence of the PDGF-B chain. Amino acid designations are in accordance with those provided by Betsholtz et al., Nature 320: 695–699 (1986), the disclosure of which is incorporated by reference. This paper gives the complete, unprocessed sequence for both the A chain and the B chain of PDGF. It is to be understood that when numbering is used herein (e.g., "Cys 123"), this refers to the complete, unprocessed sequence of the monomer; however when position is used to describe the placement of cysteine groups, e.g., "second cysteine" this refers to the processed molecule. The first amino acid in the processed PDGF A chain is serine, and is found at position 87 of the unprocessed molecule. The first amino acid in PDGF-B chain is also serine, and is found at position 81 of the unprocessed chain. Unprocessed PDGF A is 211 amino acids long; unprocessed PDGF B is 241 amino acids long.

TABLE 1

| Peptide Number | Synthesis Peptides<br>Portion of PDGF-B amino acid sequence |
|---|---|
| 1 | 154–179, but Cys at 177 changed to Ser |
| 2 | 140–162 |
| 3 | 141–162 |
| 4 | 141–178 |
| 5 | 110–139, but Cys at 123, 132 and 133 changed to Ser |
| 6 | 115–126 |
| 7 | 115–126 and 146–162 |
| 8 | 120–126 and 146–162 |
| 9 | 115–126 and 146–156 |
| 10 | 118–126 and 146–162 |
| 11 | 115–123 and 151–162 |
| 12 | 115–122 and 151–162 |
| 13 | 115–122 and 152–160 |
| 14 | 115–120 and 152–160 |
| 15 | 115–118 and 153–161 |
| 16 | 115–120 and 156–162 |
| 17 | 106–126 and 151–162 |
| 18 | 97–105 and 115–126 and 151–162 |
| *19T | 111–120 and 156–162 |
| *16 | 115–120 and 156–162 |
| *16T | 115–120 and 156–162 but tryptophan is changed to thioanisole |
| *16NPS | 115–120 and 156–162, but tryptophan is modified by nitrophenyl sulfonyl |
| *20 | Glu Ala Phe Ile Lys Trp Leu Val Arg Asn Lys Val Pro (SEQ ID NO: 10) |
| *20T | Glu Ala Phe Ile Lys Trp Leu Val Arg Asn Lys Val Pro, but tryptophan is modified by thioanisole (SEQ ID NO: 10) |

In Table 1, an asterisk means homogeneous peptide was used. Otherwise, crude peptide was used. An explanation of homogeneous and crude peptide is presented infra.

The ability of the peptides to inhibit binding of PDGF-BB was measured in terms of how much peptide was needed to decrease binding by 50%. In Table 2, "+++" means <30 μM; "++" from 30–60 μM; "+" 60–150 μM; and "−", >150 μM.

TABLE 2

| Ability To Compete With PDGF-BB For Binding | |
|---|---|
| Peptide | Inhibitory Activity |
| 1 | − |
| 2 | − |
| 3 | − |
| 4 | ++ |
| 5 | + |
| 6 | + |
| 7 | +++ |
| 8 | − |
| 9 | +++ |
| 10 | ++ |
| 11 | +++ |
| 12 | + |

TABLE 2-continued

Ability To Compete With PDGF-BB For Binding

| Peptide | Inhibitory Activity |
| --- | --- |
| 13 | + |
| 14 | + |
| 15 | − |
| 16 | +++ |
| 17 | +++ |
| 18 | +++ |
| *19T | +++ |
| *16 | − |
| *16T | +++ |
| *16NPS | +++ |
| *20 | − |
| *20T | − |

While only results for PDGF-BB inhibition are shown, similar results were obtained when PDGF-AA was used.

The peptides tested were all derived from the region spanning amino acids 97–180 ("Cys—Cys") of PDGF-B, because this region has been found to be sufficient to impart the full biological activity of the molecule. (King et al., Proc. Natl. Acad. Sci. USA 82: 5295–5299 (1985)).

Co-linear peptides 1–6 yielded only limited inhibition. The weak inhibition secured with peptides 4 and 5 suggested that the combination of these two regions of the sequence might be more effective.

Peptide 7, 29 amino acids long and containing 12 N-terminal region and 17 C-terminal amino acids, competed efficiently for both receptors, with 50% competition at abut 6 μM. In view of these results, additional peptides were prepared and tested so as to narrow the epitopes involved. Peptide 8, in which the five most N-terminal amino acids of peptide 7 were deleted, was nearly devoid of activity, as was peptide 9, lacking the six most C-terminal amino acids. When three amino acids at the N-terminal side of the epitopic junction were removed (peptide 10), or five C-terminal amino acids were removed (peptide 11), the effect on activity was lessened.

Attempts to further define the two epitopes led to the generation of peptide 16, which has amino acid sequence Ala Asn Phe Leu Val Trp Glu Ile Val Arg Lys Lys Pro (SEQ ID NO: 3)

and maintained most of the receptor competing activity. Removal of two junction amino acids, however, yielded an insoluble peptide which could not be analyzed. Extensions at the $NH_2$-terminus (peptides 17–19), did not increase activity. The conclusion reached from these experiments is that a peptide, 13 amino acids long and containing portions of two regions of B chain of PDGF, is an efficient competitor of PDGF-AA and PDGF-BB binding to the α and β receptors.

Example 2

The peptides used in the experiments of Example 1 had been prepared using t-Boc chemistry using a peptide synthesizer. They were cleaved from polymeric supports via incubation with HF at 0° C. for 60 minutes with 8% anisole and 4% methyl ethylsulfide as scavengers. When peptides contained tryptophan, 3% thioanisole was added. These preparations were crude formulations.

The interesting results secured with peptide 16 suggested experiments using purified material. To that end, peptide 16 was purified via reversed phase HPLC on a Vydac C18 column (10×250 mm) using a 30 minute gradient of 10–90% acetonitrile in 0.1% trifluoroacetic acid. Peptide was identified and analyzed using $^{252}Cf$ plasma desorption mass spectrometry, as per Sundqvist et al., Mass Spectrometry Rev. 4: 421–460 (1985). Each fraction from the HPLC was then analyzed, both via the methodology described supra, and via mass spectrometry.

Figure 1:
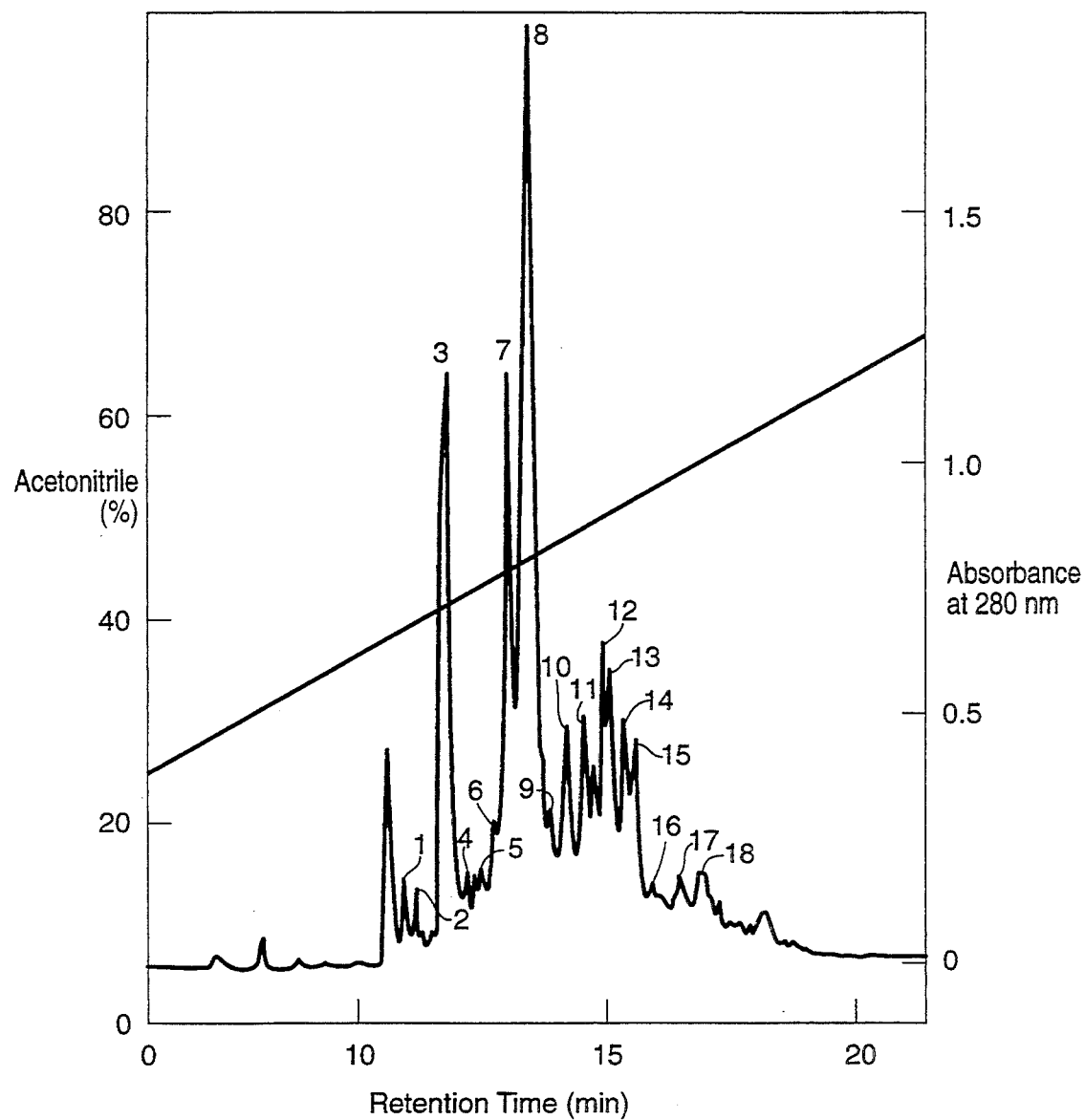
FIG. 1 shows HPLC purification of peptide 16T, which is elaborated upon in the examples.
Figure 2:
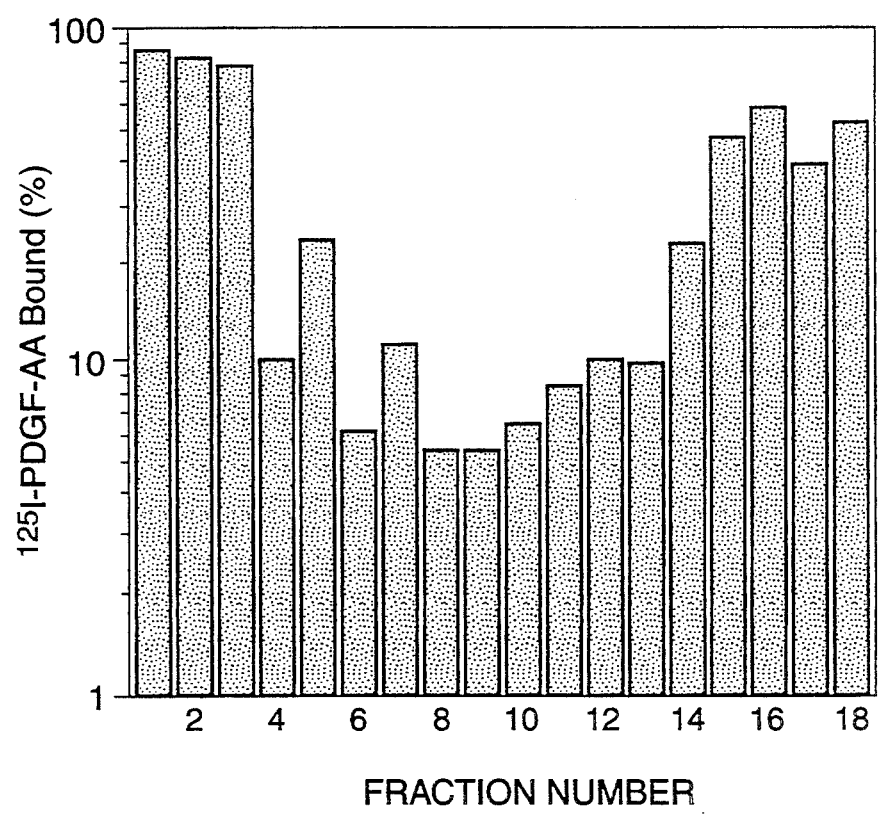
FIG. 2 shows competitor activity of peptides on $^{125}$I-PDGF-AA binding to α receptors.

Surprisingly, the component with the expected molecular mass of peptide 16 ("16*" in Tables 1 and 2), had very low activity compared to other HPLC components. A component showing a molecular mass of 122 Da, which is greater than that of peptide 16, showed higher activity. Analysis of the HPLC work led to the conclusion that thioanisole had been attached to tryptophan in peptide 16 during mass spectrometry. To secure larger amounts of this peptide, referred to as "16T", higher concentrations of thioanisole were used in the deprotection step. HPLC purification is shown in FIG. 1, and the competitor activity of the various HPLC fractions are shown in FIG. 2. Table 3, which follows, presents proposed structures and masses of ions determined by HPLC.

TABLE 3

Mass spectrometric analysis of fractions collected during HPLC purification of Peptide 16.

| Fraction | Observed m/z | Proposed molecule (Expected value of m/z within parentheses) |
| --- | --- | --- |
| 1 | 1452.6 | M—Phe (1453.7) |
|  | 1581.6 | M Nitril (1582.9) |
| 2 | 1601.0 | M (1600.9) |
|  | 1581.5 | M Nitril (1582.9) |
| 3 | 1599.2 | M (1600.9) |
| 4 | 1485.8 | M—Asn (1486.8) |
|  | 1599.2 | M (1600.9) |
|  | 1644.9 |  |
| 5 | 1644.8 |  |
|  | 1560.0 |  |
| 6 | 1574.0 | M122-Phe (1575.9) |
|  | 1654.9 | M + tBu (1657.0) |
| 7 | 1708.1 | M122 Nitril (1705.8) |
| 8 | 1721.2 | M122 (1723.1) |
| 9 | 1754.0 | M + Tos (1755.1) |
|  | 1722.8 | M122 (1723.1) |
|  | 1689.9 | M + OBzl (1691.0) |
|  | 1651.1 | M122-Ala (1652.0) |
|  | 1594.2 | M1222-Lys/Glu (1594.1/1593.9) |
| 10 | 1724.7 | M122 (1723.1) |
|  | 1608.5 | M122-Asn (1609.0) |
| 11 | 1763.9 | M122 Nitril + tBu (1761.2) |
| 12 | 1778.1 | M122 + tBu (1779.2) |
| 13 | 1778.1 | M122 + tBu (1779.2) |
| 14 | 1846.9 | M122 + Clz (1847.6) |
|  | 1875.8 | M122 + Tos (1877.3) |
| 15 | 1847.0 | M122 + Clz (1847.6) |

Abbreviations: M, Peptide 16; M122, Peptide 16T; Nitril, dehydrated asparagine; tBu, tert-Butyl; Tos, 4-toluendesulfonyl; OBzl, Benzyl ester, Cl-z, 2-chlorobenzyloxycarbonyl.

Example 3

To test the hypothesis that modification of tryptophan would potentiate activity, peptide 16 was incubated with 2-nitrophenylsulfenyl chloride (NPS-Cl), which is known to react with tryptophan (see Scoffone et al., Biochem. 7: 971–979 (1968)). The resulting derivative "16NPS", also had increased activity as an antagonist as compared to peptide 16.

Figure 3A:
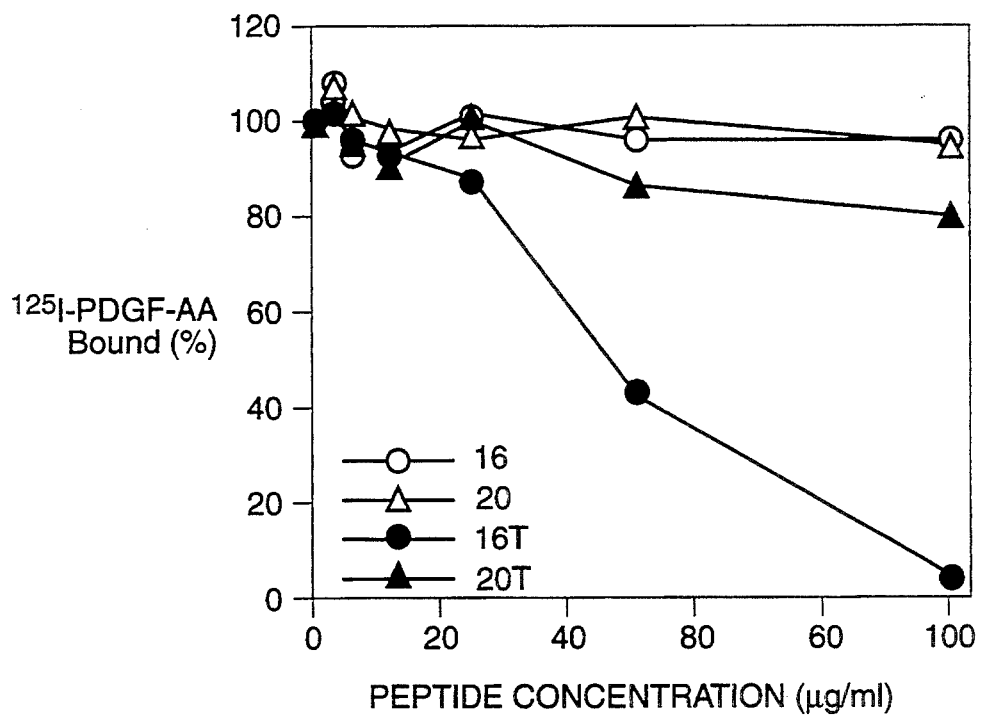
Figure 3B:
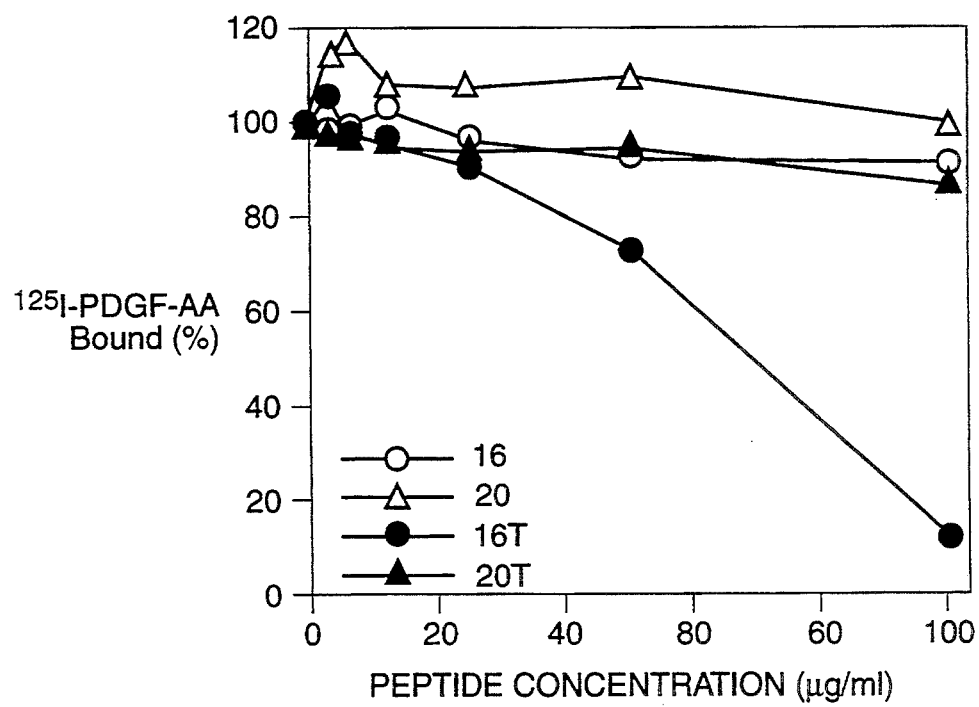

In comparative experiments, depicted in FIGS. 3A, 3B and 3C, peptides 16 and 16T were tested for competitive activity for both $^{125}I$-PDGF-AA and $^{125}I$-PDGF- BB (α and β receptors). The figures show that while peptide 16 had a marginal effect, 16T was an effective competitor for both PDGF-AA and PDGF-BB. Forty-four ug/ml (26 μm), and 57 ug/ml (33 μM) of peptide 16T gave 50% competition for receptor binding to $^{125}$I-PDGF-AA and $^{125}$I-PDGF-BB, respectively.

A control was carried out using peptides with randomized amino acid sequence—i.e., peptides 20 and 20T, the latter carrying the thioanisole modification on tryptophan. As shown in FIGS. 3A, 3B and 3C, the peptides did not compete for binding. The conclusion which must be reached from these experiments is that the amino acid sequence and a tryptophan modification are important for competitive behavior.

FIG. 3C shows that none of peptides 16, 16T, 20 and 20T compete for binding of $^{125}$I-EGF to the EGF receptor. The peptide 16T thus is specific for PDGF receptor competition.

Example 4

The possible role of peptide 16T as an antagonist for PDGF activity in vivo was investigated. Following the methodology of Betsholtz et al., J. Cell Physiol 118: 203-210 (1984), the disclosure of which is incorporated by reference, [$^3$H] thymidine incorporation by human fibroblasts in the presence of various peptides was studied. Table IV shows these results infra. Table IV shows that PDGF-BB and EGF stimulated the incorporation of [$^3$H] thymidine into fibroblasts 4- and 5-fold, respectively. PDGF-AA gave lower stimulation, which is consistent with the results obtained by Nisler et al., Cell 52: 791-799 (1988). The peptides 16 and 16T did inhibit PDGF-AA and PDGF-BB induced mitogenicity, but also EGF induced mitogenicity. This indicates that peptides 16 and 16T did not operate solely on the level of competition for receptor; rather, an additional mechanism is involved. Peptide 20, i.e., the control, showed a minor effect on ligand stimulated [$^3$H] thymidine incorporation, while peptide 20T showed some non specific inhibition activity. Peptide 16T was more efficient than peptide 16, and lowered background incorporation of [$^3$H] thymidine dramatically.

TABLE 4

Effect of the Peptide 16, 16T, 20 and 20T on ligand stimulated [$^3$H]thymidine incorporation in human foreskin fibroblasts. Figures represent mean of duplicates.

| Peptide | Control (cpm) | Ligand used for stimulation | | |
|---|---|---|---|---|
| | | PDGF-AA (cpm) | PDGF-BB (cpm) | EGF (cpm) |
| Control | 483 | 677 | 1918 | 2591 |
| Peptide 16 | 241 | 242 | 281 | 216 |
| Peptide 20 | 348 | 535 | 1541 | 2059 |
| Peptide 16T | 46 | 90 | 102 | 119 |
| Peptide 20T | 456 | 489 | 836 | 515 |

Example 5

Further experiments were carried out to study the effect of the peptides on intact cells; specifically, inhibition of ligand degradation was studied.

To do this, confluent human foreskin fibroblast cells in 12 well dishes were washed once with 1.0 ml of Ham's F-12 medium, supplemented with 1 mg/ml BSA. As described supra, those cells to be tested later for $^{125}$I-PDGF-BB degradation were preincubated with PDGF-AA to down regulate α receptors. Cells were then incubated with different concentrations of each of peptides 16, 16T, 20 and 20T together with $^{125}$I labelled PDGF-AA, PDGF-BB or EGF in 0.5 ml/well Ham's F-12 medium containing 1 mg/ml BSA. The mixtures were incubated for four hours at 37° C., the incubation medium was removed, and then precipitated with trichloroacetic acid at 10% final concentration. The amount of trichloroacetic acid non-precipitatable radioactivity in cell culture medium was taken as an estimate of ligand degradation—i.e., it represents ligand that had been internalized, degraded and released into the medium in the form of free $^{125}$I, $^{125}$I-Tyr or low molecular weight fragments. This parameter was defined after four hours of incubation at 37° C.

Figure 4B:
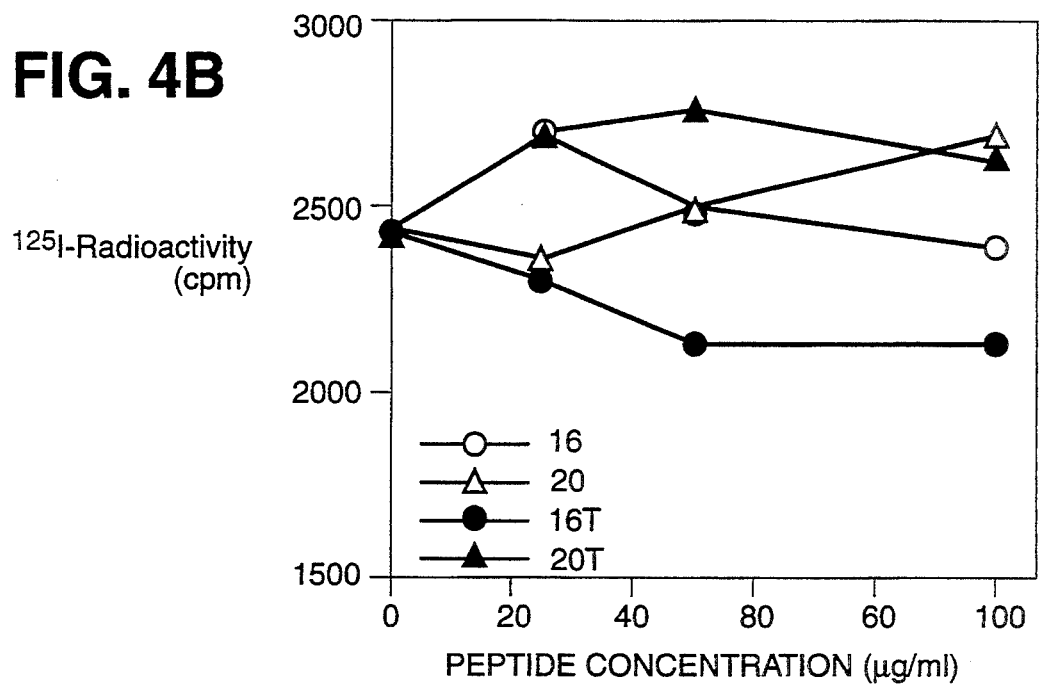
Figure 4C:
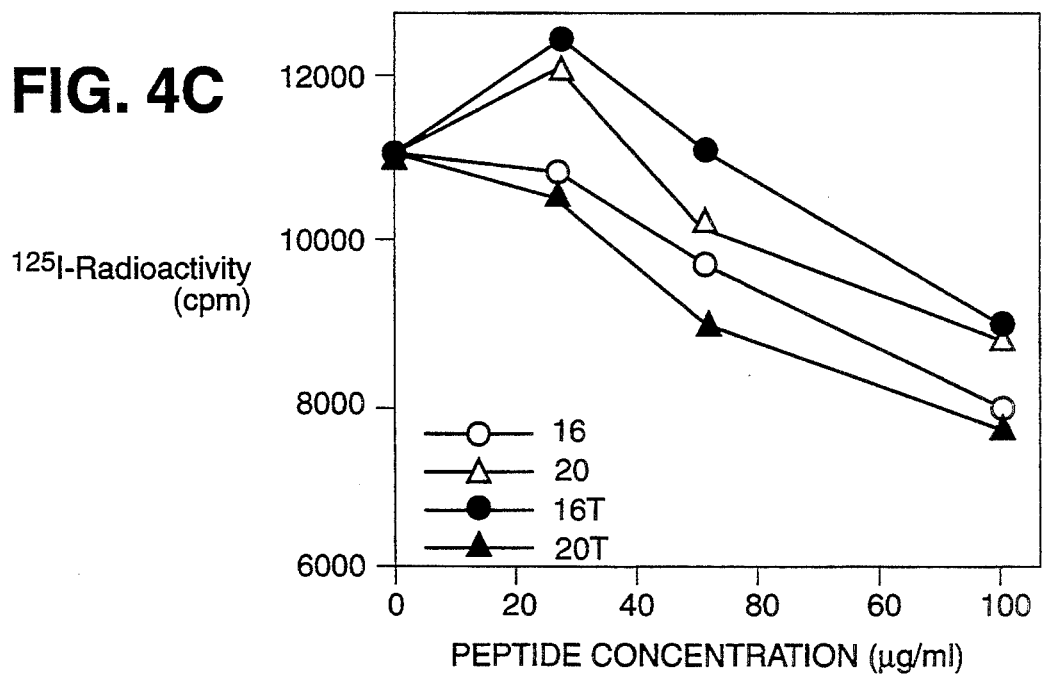

FIG. 4 shows that all peptides showed some inhibitory activity with respect to $^{125}$I-PDGF-AA degradation, with peptide 16T being the most effective. The effect on PDGF-BB degradation was lower, with peptide 16T being the most potent. All peptides inhibited $^{125}$I-EGF degradation, but all peptides showed a similar activity.

These results show that peptide 16T has an effect on cells which is a combination of specific inhibition at PDGF receptor level and an effect inside the cell which is not PDGF specific.

Example 6

The foregoing results show that peptide 16T interacts with both the α and β receptors. As binding of PDGF to receptors leads to receptor internalization and down regulation, investigations were carried out to determine whether the interaction of PDGF and peptide 16T led to the internalization and down regulation of receptors. To test this, confluent cells, as described supra, were washed once with binding buffer at 37° C., followed by incubation with different concentrations of synthetic peptide (0.5 ml of PBS containing 1 mg/ml BSA). Following this, the cells were incubated at 37° C. for four hours, followed by washing with 1 ml of ice cold buffer consisting of 20 mM Na-acetate, 150 mM NaCl, 0.2% BSA adjusted to pH 3.7 with acetic acid. The cells were then incubated for 10 minutes on ice in buffer, followed by two washings with 1 ml binding buffer, at pH 7.4. The number of PDGF receptors on the cell surface was estimated by incubation with $^{125}$I-PDGF-BB (~50,000 cpm) in 0.5 ml binding buffer for 60 minutes on ice, followed by washing, lysis and determination of cell bound radioactivity.

Results were negative—i.e., peptide 16T did not downregulate the PDGF-α or β receptors.

Example 7

Studies were carried out to determine if the interaction of peptide 16T with PDGF receptors was agonistic or antagonistic. This involved the study of dimerization and autophosphorylation of PDGF and EGF receptors in intact cells.

Confluent human foreskin fibroblast cells were used (25 cm$^2$ dishes of cultures). The cells were washed twice with binding buffer, as described supra, with 1 mg/ml BSA added thereto. This was followed by 90 minutes of incubation with one of synthetic peptides 16, 16T, 20 and 20T on ice. This was followed by the addition of either PDGF-BB or EGF (300 ng/ml) and 60 minutes of further incubation. A dimerization assay was then carried out, basically following Eriksson et al., Growth Factors 6: 1-14 (1992). Essentially, receptors were cross linked for 20 minutes at room temperature in 1 mM BS$^3$ (Bis(sulfosuccinimidyl)suberate) in lysis buffer (0.5% Triton X-100, 0.5% deoxycholate, 20 uM Hepes, pH 7.4, 150 mM NaCl, 10 mM EDTA, 1 mM PMSF (phenylmethylsulfonyl fluoride), 1% Trasylol (aprotinin), 100 μM ortovandat, a phosphatase inhibitor). Cross linking was quenched by adding 70 mM methylammonium chloride for 10 minutes. Samples were then subjected to SDS gel electrophoresis in 4% slab gels, followed by electroblotting on to nitrocellulose membranes. The blocked membranes were incubated for two hours with affinity purified phosphotyrosine antibodies (Ek et al., J. Biol. Chem. 259: 1145–11152 (1984)), followed by three washes. Blots were then incubated for 45 minutes with peroxidase conjugated, affinity purified swine antirabbit IgG immunoglobulin. After an additional three washes, complexes were visualized using the ECL developing system.

Figure 5:
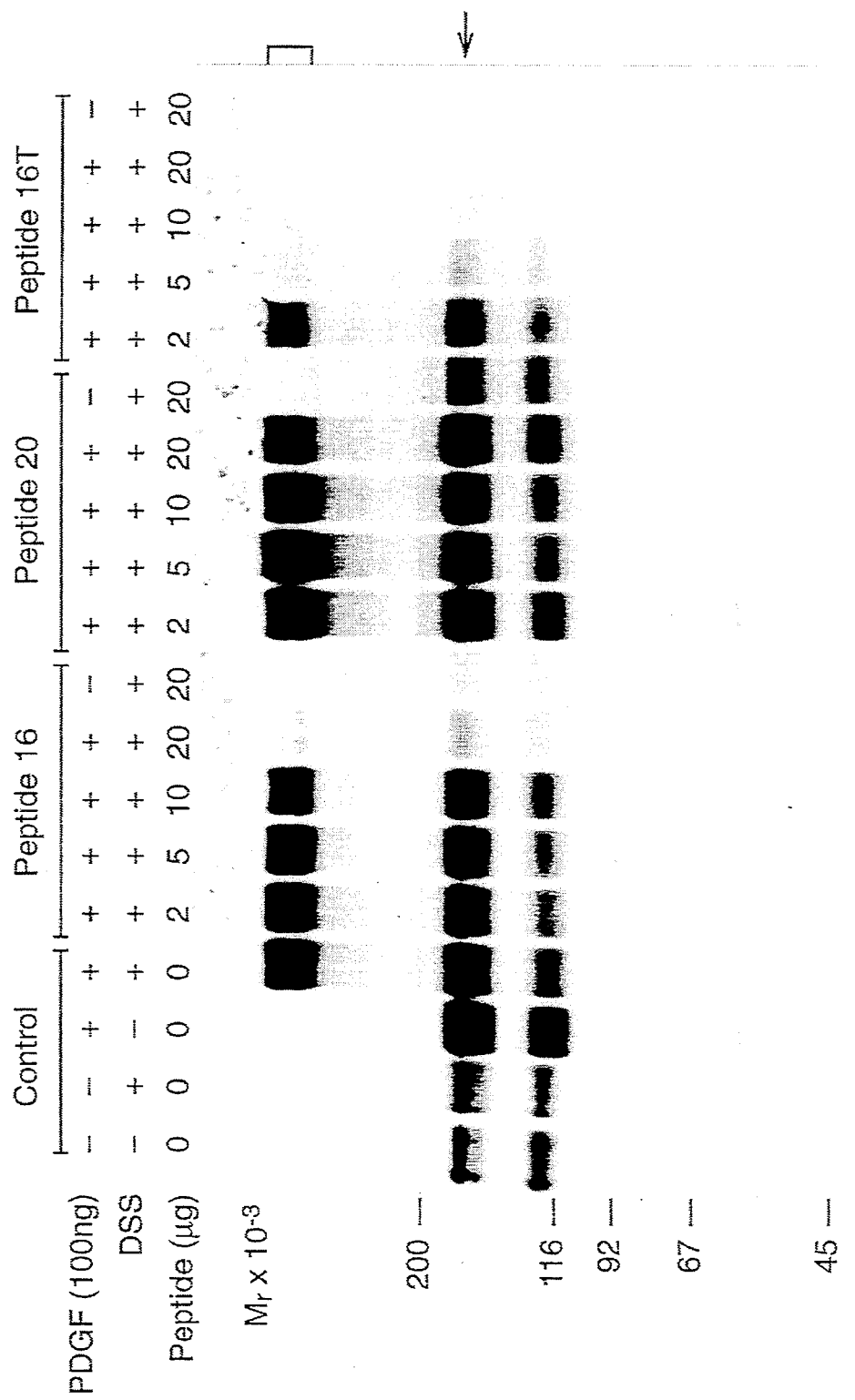
FIG. 5 shows the inhibition of receptor dimerization and autophosphorylation by peptide 16T.

The results, presented in FIG. 5, show that both PDGF and EGF induced autophosphorylation of receptors. After cross linking, most of the autophosphorylated receptors were visualized as fuzzy, double sized components (bracket of FIG. 5), probably representing dimers.

When peptide 16T was used, PDGF induced autophosphorylation and dimerization was inhibited by about 55%. There was no effect on EGF induced activity. Control peptide 20T showed no effect whatsoever. These results show that peptide 16T is an antagonist, rather than an agonist.

Example 8

Further experiments were carried out involving autophosphorylation and dimerization. These were more quantitative, as they used partially purified PDGF-β receptors.

A preparation of PDGF-β receptor, from Triton X-100 solubilized porcine uterus membranes and purified up to the Mono-Q chromatography step of Rönnstrand et al., J. Biol. Chem. 262: 2929–2932 (1987), was made, and the autophosphorylation assay described therein was carried out.

Approximately 100 ng of the receptor was incubated for 5 minutes at 0° C. with peptide 16T or peptide 20, at different concentrations. PDGF-BB (100 ng) was added and incubated for another 15 minutes. Incubation mixtures had a total volume of 40 ul and contained, as final concentration, 0.1% Triton X-100, 5% glycerol, 0.5 mM EGTA, 0.5 mM dithiothreitol, 20 mM Hepes, pH 7.4, 180 mM NaCl, 3 mM $MnCl_2$, and 1 mg/ml BSA. Four ul of 150 μM [$^{32}P$]ATP (containing $5 \times 10^6$ cpm of radioactivity) was added, followed by an additional 10 minutes of incubation at 0° C. Incorporation of radioactivity was terminated by adding 5 μl of 15 mM unlabelled ATP and 5 μl of 40 mM phenylphosphate. Samples were cross linked by incubating with 0.5 mM DSS (12.5 mM, in dimethyl sulfoxide) for 30 minutes at room temperature. The cross linking reaction was blocked by adding 50 mM methylammonium chloride, 20 mM Hepes, pH 7.4.

In the absence of peptide, PDGF induced autophosphorylation of its 180 KDa receptor and a 130 KDa degradation product, as shown in FIG. 5. Following covalent cross linking, most autophosphorylated material was seen as a double band at about 350 KDa.

When peptide 16T was present, as concentrations increased, both dimerization and autophosphorylation decreased. Nearly complete inhibition was obtained at 5 μg of peptide. Control peptide 20 showed no effect at concentrations up to 20 μg. Peptide 16 had an intermediate effect, with complete inhibition at 20 μg. These results parallel those obtained in the studies of ligand binding inhibition, discussed supra.

Example 9

Prior work has shown that each PDGF strand contains eight cysteine residues, but free SH groups have not been found. (Claesson-Welsh et al., Proc. Natl. Acad. Sci. USA 86: 4917–4921 (1989)). It was suspected that PDGF most probably contains an even number of interchain disulfide bridges, most likely two interchain bridges, and three intrachain bridges in each subunit. It was thought that interchain disulfide bridges might be more susceptible to reduction than the interchain disulfide bonds. In order to attempt to identify interchain bonds, partial reduction methodologies were employed.

Aliquots of recombinant PDGF-AA long splice variant were incubated with different concentrations of dithiothreitol ("DTT") for two hours at room temperature. These samples were then alkylated and analyzed by SDS-gel electrophoresis, using non reducing conditions. Silver staining followed.

Figure 6:
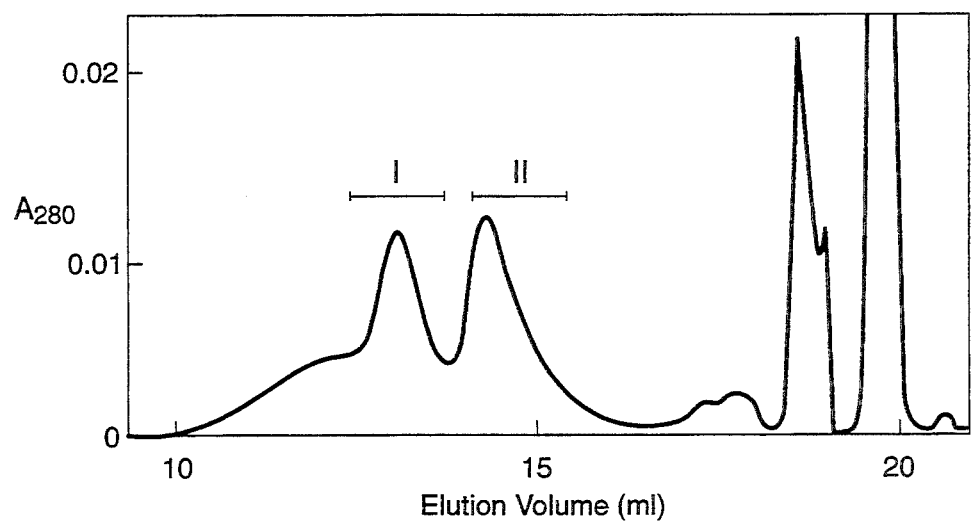
FIG. 6 shows the effect of the reducing agent dithiothreitol ("DTT") on dimeric PDGF-AA.
Figure 6A:
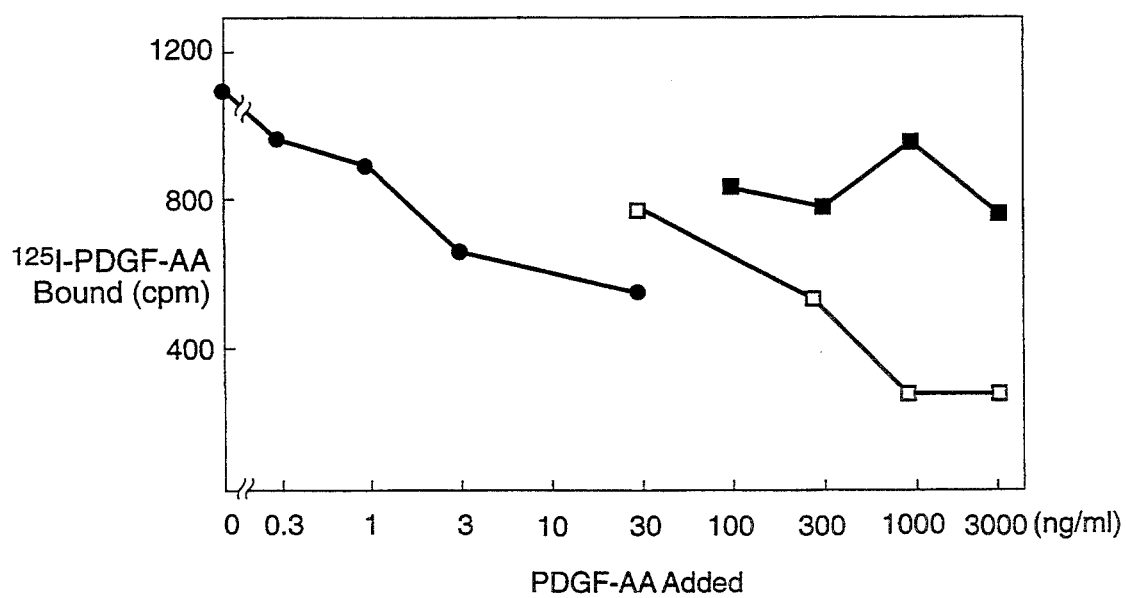
FIG. 6A shows elution of bound 125I-PDGF-AA when PDGF-AA was added.
Figure 6B:
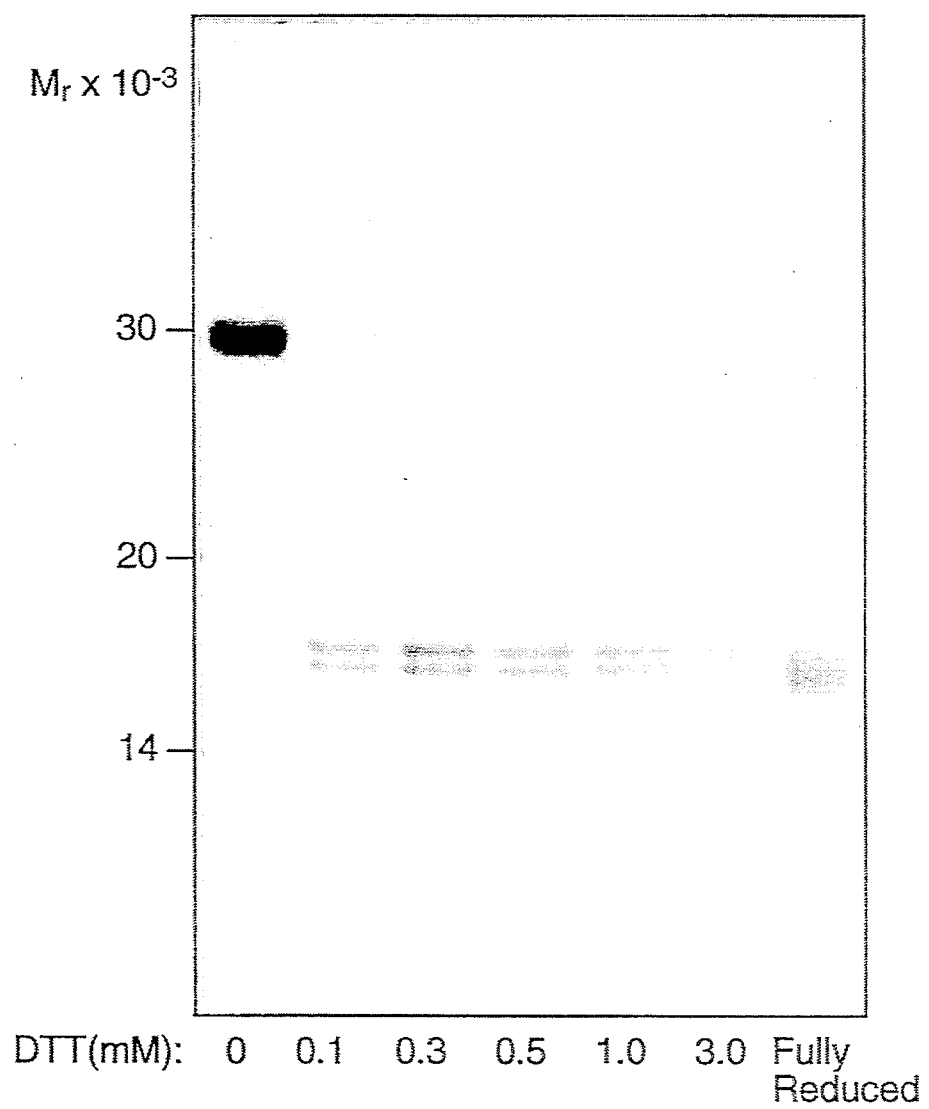
FIG. 6B shows the elution of monomeric materials following reduction of dimeric PDGF.

FIG. 6B shows that PDGF-AA gradually shifted from 30 KDa to 17 KDa—a shift from dimer to monomer—as the concentration of DTT increased. At 3 mM DTT, almost all PDGF appeared as a monomer, but the material migrated more slowly than fully reduced PDGF, suggesting the intrachain bonds remained.

This experiment confirmed that interchain bonds are more susceptible to reduction than intrachain bonds, and suggests that the use of this methodology could identify the particular residues involved.

Example 10

The experiment of Example 9 was carried out on a preparative scale. 90 μg of recombinant, long splice PDGF-AA was treated with 3 mM DTT in 220 μl of 0.36M Tris.HCl, pH 8.2 for two hours at 20° C. This exposed interchain SH bonds, which were then reacted with 9 mM iodoacetic acid in the same solution for 15 minutes to alkylate the groups. The alkylated monomers were isolated by gel chromatography on Superose 12 (1×30 cm) in 6M urea, 0.3M NaCl and 1M acetic acid at a flow rate of 15 ml/h. Two peaks eluted, as shown in FIG. 6. The fractions were analyzed via SDS-gel electrophoresis following Blobel et al., J. Cell Biol. 67: 835–851 (1975), followed by silver staining. The gel work showed that the two HPLC fractions were monomers and dimers. Monomeric material was isolated by desalting via reversed phase HPLC using a narrow bore Brownlee Aquapore C1 column. The material was divided into two portions. One was used in receptor binding assays, the other was fully reduced. The experiments on these two fractions follow, those involving full reduction being presented first. Receptor binding was carried out using the protocols of Example 14, infra.

Example 11

The partially reduced, monomeric PDGF-A was fully reduced by 20 mM DTT in 4M guanidine-HCl, 1M Tris.HCl, pH 8.0 and 10 mM EDTA for two hours at 37° C. This fully reduces the monomers, which were then treated with 4-vinylpyridine (incubation for two hours, room temperature). The reduced monomers were desalted, as described supra and dried. The treatment with 4-vinylpyridine pyridylethylates cysteine residues, rendering them visible at 254 nm.

Reduced material was digested with Glu-C protease at an enzyme/substrate ration of 1/50 (w/w) for 15 hours at 37° C. in 200 ul of 2M urea and 0.1M ammonium bicarbonate. At the end of the reaction time, the mixture was applied to a Brownlee Aquapore C4 (2.1×30 mm) narrow bore column, and fragments were eluted by a linear gradient of n-propanol (0–27% over 60 minutes) 0.16% trifluoroacetic acid at a flow rate of 100 ul/min. Effluent was monitored using a photodiode array detector, and spectral data were collected between 200 and 300 nm.

Figure 7A:
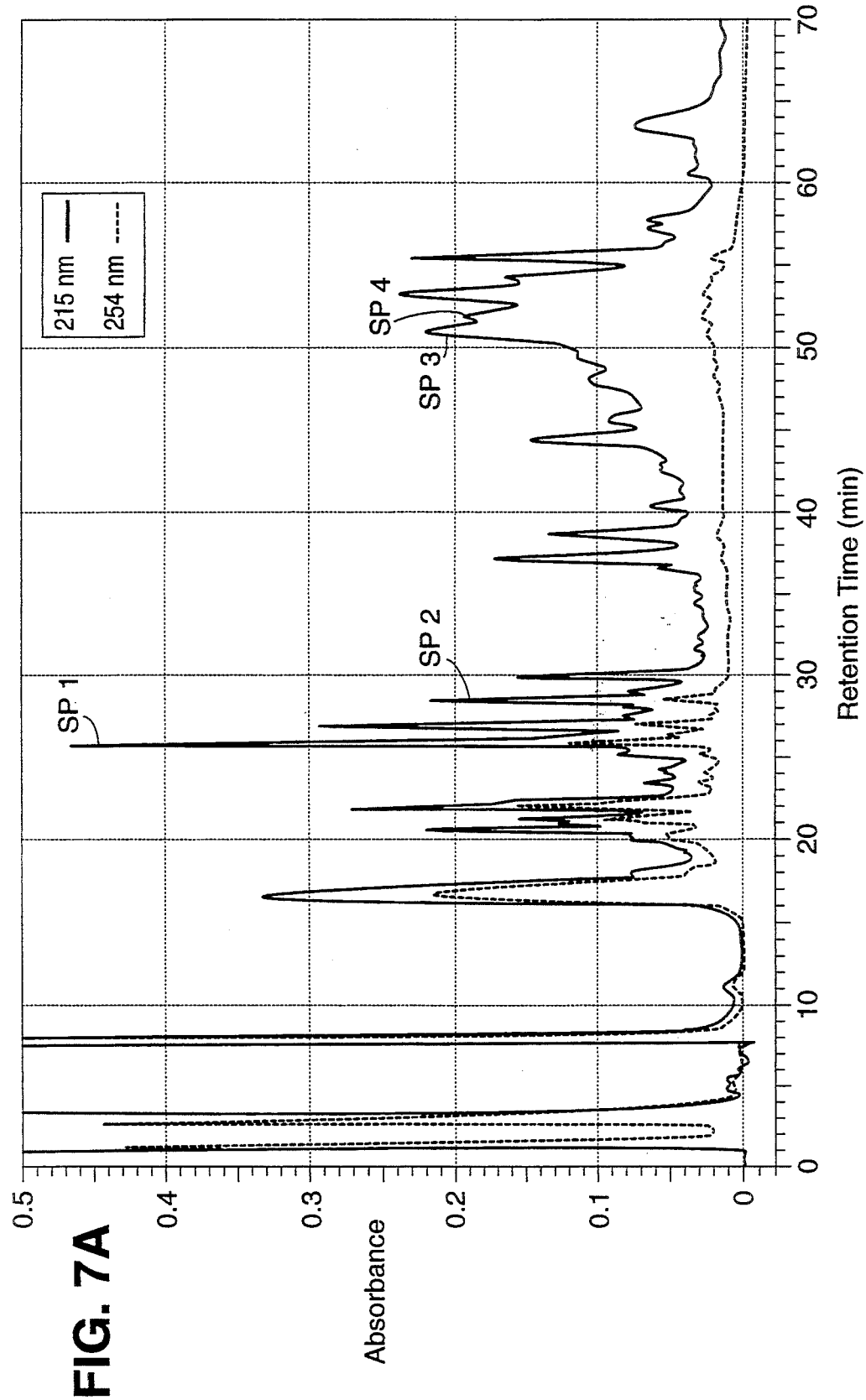
FIG. 7A shows HPLC information secured from proteolytically degraded, partially reduced monomeric PDGF-A.
Figure 7B:
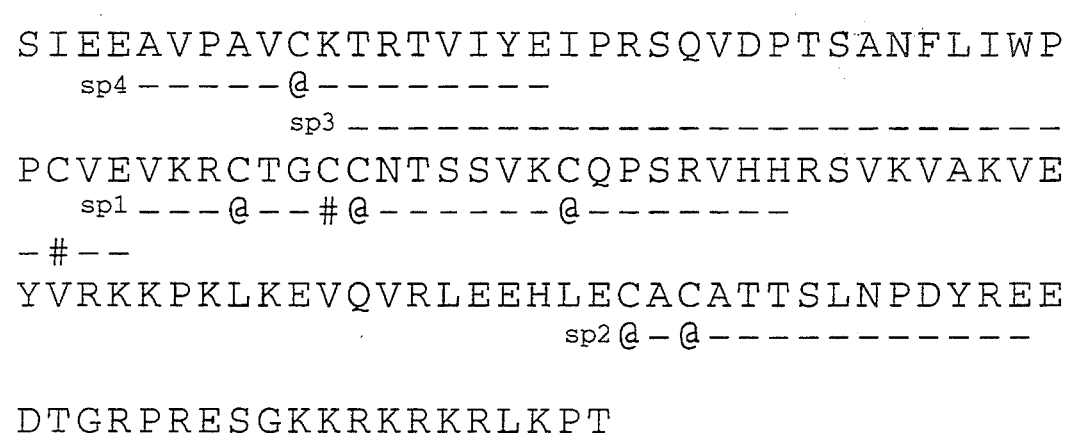

These HPLC fractions were dried ,onto polybrene treated glass fiber discs and subjected to well known Edman degradation. HPLC information is presented in FIG. 7A. The sequences which were found to contain cysteine residues are shown in FIG. 7B (i.e., sequences SP1, 2, 3 and 4). The amino acid sequence, i.e., the top line, is set forth in SEQ ID NO: 7. In FIG. 7B, the "#" is a carboxymethyl cysteine, and "@" is a pyridylethyl cysteine.

Those cysteine residues involved in interchain disulfide bonds should appear as carboxymethyl cysteine, due to the action of iodoacetic acid, while intrachain bond forming cysteine should appear as pyridylethylcysteine. These results show that the 2nd and 4th cysteine residues in the PDGF-A monomer form the interchain, disulfide bounds.

Example 12

In order to pursue the results of Example 11 further, cDNA sequence coding for a PDGF molecules were mutated so that Cys 123 and Cys 132 were serine. To do this, cDNA for the short splice version of PDGF-A (Betsholtz et al., Nature 320: 695–699 (1986)) was used. Following Kunkel et al., Meth. Enzymol 154: 367–382 (1987), codons corresponding to one or both of the residues, resulting in pSV Ser 2, pSV Ser 4, and pSV monoA were produced. A uracil containing template coding for wild type PDGF-A was also produced. Similarly, corresponding codons in the B chain cDNA (Cys 124, Cys 133 of the PDGF B stop variant) were mutated to yield pSV monoB, together with conversion of codon 191 to a stop codon, thereby yielding a soluble product (Ö stman et al., Cell Reg. 2: 503–512).

To produce the vectors pSV monoA, pSVA Ser 2 and pSV Ser 4, mutated fragments were cloned into the EcoRI/Bal 1 sites of vector pSV-PDGF-A 102A (pSVA), as taught by Ö stman et al., J. Bio. Chem. 263: 16202–16208 (1988), in which wild type fragments were excised. The construct pSV monoB was generated by cloning into the EcoRI site of plasmid pSV7d. This plasmid is well known and its structure is given in Truett et al., DNA 4(8): 333–349 (1985), FIG. 2. It is also presented as FIG. 12.

Example 13

The constructs of Example 12, including pSVA and pSVB stop were transfected into COS cells following Östman et al., Cell Reg. 2: 503–512 (1991), using 20 ug of plasmid DNA and 0.5—1×$10^6$ cells in 60 mm culture dishes. Two days after transfection, metabolic labeling was performed. This was accomplished by growing cells overnight in 1.5 ml of cysteine free MCDB 104 medium, supplemented with 0.1 mCi [$^{35}$S] cysteine/ml, 10% dialyzed fetal calf serum, and antibiotics. After labelling, media were collected and cleared of cell debris via centrifugation. Cells were washed once in PBS, collected by scraping, and lysed in 0.5 ml of 0.5M NaCl;, 20 mM Tris.HCl, pH 7.5, 0.5% Triton X-100%, 1% aprotinin, and 1 mM PMSF. Cell lysates were centrifuged for 15 minutes at 10,000 g, and supernatants subjected to immunoprecipitation using antiserum to PDGF-AA. Essentially, the samples were precleared by incubation with 15 ul of normal rabbit serum at 4° C. for 1 hour, followed by addition of 60 ul of a 50% Protein-A-Sepharose slurry in PBS. This was incubated at 4° C. for 30 minutes, and beads were removed by centrifugation. Following this, 15 ul of anti PDGF AA or anti-PDGF BB were added, followed by two hours of incubation at 4° C. This was again followed by incubation with Protein A Sepharose (supra). The beads were then washed five times with 0.5M NaCl, 20 mM Tris, pH 7.5, 5 mg/ml BSA, 1% Triton X-100 and 0.1% SDS, as well as once with 20 mM Tris-HCl, pH 7.5. Immunocomplexes were eluted by adding 200 ul of nonreducing sample buffer, with three minutes of incubation at 95° C. Half of the eluted material was reduced by adding DTT (final concentration, 10 mM), and two minutes of incubation at 95° C. Alkylation was carried out with 50 mM final concentration iodoacetamide. Samples were analyzed by SDS gel electrophoresis, using 12–18% polyacrylamide gels and fluorography.

Results are shown in FIGS. 8A and 8B. FIG. 8A shows that when conditioned medium from [$^{35}$S]-cysteine labelled cells was immunoprecipitated, only monomeric forms were found. When analyzed under reducing conditions, the PDGF mono A shifted in the gel, indicating that intrachain disulfide bonds were present. Also, anti-wild type PDGF-AA antiserum recognized PDGF mono-A, supporting the theory that the conformation of PDGF mono A is similar to the two chains in the dimer.

The parallel mutant, PDGF mono B showed the same pattern of analysis, as will be seen in FIG. 8B.

Example 4

The following experiments describe receptor binding assays using the recombinant proteins produced following Example 13.

In the case of recombinant proteins, thirty six hours after transfection, culture medium was changed to 1.5 ml of serum free medium, and culture continued for 48 hours. Media were then applied onto a narrow bore, reversed phase C4 HPLC column (2.1×30 mm) for desalting and concentration. The column was washed with 0.1% trifluoroacetic acid, and retained material eluted with 70% acetonitrile in 0.1% trifluoroacetic acid. After evaporation, samples were dissolved in one tenth of the original volume of PBS, and binding to PDGF-α and β receptors was studied. The study was carried out by analyzing serial dilutions and their ability to compete with $^{125}$I-PDGF-AA and $^{125}$I-PDGF-BB for binding to AG-1518 cells. Cells had been grown in Falcon 24-well plates to confluence, followed by one washing in binding buffer (PBS with 1 mg/ml BSA, 0.9 mM CaCl$_2$, 0.5 mM MgCl$_2$). Cultures were incubated at 0° C. for two hours in 200 ul of binding buffer containing the different dilutions as shown in FIG. 9, or known amounts of PDGF-AA or PDGF-BB for standardization. Cells were washed twice with binding buffer, after which radiolabelled PDGF-AA or PDGF-BB (0.5–2 ng; 15,000–30,000 cpm) in 200 ul binding buffer was added. This was incubated at 0° C. for one hour, after which cells were washed five times with binding buffer, followed by lysis in 200 ul of 20 mM Tris.HCl, pH 7.5, 1% Triton X-100 and 10% glycerol, at room temperature for 20 minutes. Solubilized $^{125}$I radioactivity was measured in a geiger counter.

Where β-receptor assays were carried out, prior depletion as discussed supra, was also used.

The results, as presented in FIG. 9, show monoB competed relatively well. Data are not shown for PDGF monoA, which did not detectably bind to the α receptor.

Example 15

It was important to determine whether the binding of monomeric PDGF to PDGF receptors induced agonistic or antagonistic effects. The PDGF-mono B molecule was therefore tested for its ability to activate β-receptor in an autophosphorylation assay. Conditioned media from cultures of COS cells transfected with pSV B stop, pSV monoB or from mock transfected cells were desalted and concentrated as described supra. A radio receptor assay was carried out to determine receptor binding activity, using standard techniques. Once this was accomplished, media from pSV monoB or pSV monoB stop transfected cells were adjusted with mock transfected medium to receptor binding activity of 100 ng/ml. PAE cells expressing PDGF B receptors (Westermark et al., Proc Natl. Acad. Sci. USA 87: 128–132 (1990)), grown in 25 cm$^2$ dishes were labeled in serum and methionine free MCDB 104 medium supplemented with 0.1 mg/ml BSA and 0.1 ml [$^{35}$S] methionine/ml for three hours at 37° C. Cells were stimulated with 1 ml of different concentrations of conditioned media for 30 minutes at 4° C. A positive control was set up using 1 ml of mock transfected medium with 100 ng/ml of recombinant PDGF-BB. Cells were washed once with PBS, scraped into a lysis buffer of 20 mM Tris.HCl, pH 7.5, 150 mM NaCl, 10 mM EDTA, 0.5% deoxycholate, 0.5% Triton X-100, 30mM pyrophosphate, 1% aprotinin and 1 mM PMSF, followed by centrifugation for 15 minutes at 10,000 g for clearance. Half of this lysate was incubated at 40° C. for two hours with 5 ul of antiserum against a peptide derived from the PDGF-β receptor (Claesson-Welsh et al., J. Biol. Chem. 264: 1742–1747 (1989)); the other half with 1 ul of antiserum against phosphotyrosine (Ek et al., J. Biol. Chem. 259: 1145–11152 (1984)). Immunocomplexes were precipitated with 60 ul of a 50% slurry of Protein-A-Sepharose in PBS, after which beads were washed three times with lysis buffer, twice with 20 mM Tris.HCl, pH 7.5, 0.5M NaCl, 1% Triton X-100, and once in distilled water. Elution of immunocomplexes was performed by adding 100 ul of sample buffer containing 4% SDS, 0.2 mM Tris.HCl, pH 8.8, 0.5M sucrose, 5 mM EDTA, 0.01% bromophenol blue and 2%-mercaptoethanol. Immunocomplexes were analyzed by SDS-gel electrophoresis, using a 7% acrylamide gel and fluorography.

FIGS. 10A and 10B show these results. In FIG. 10A, analysis of immunoprecipitates using SDS-gel electrophoresis shows that both pSVB stop and pSV monoB stimulated autophosphorylation. In order to determine whether PDGF-mono B caused dimerization of the receptor, the β receptor expressing PAE cells were labeled with [$^{35}$S] methionine and stimulated with concentrated conditioned media from COS cells transfected with either of the relevant constructs. In these experiments, the labeled PAE cells were incubated for 90 minutes at 4° C., with 1 ml portions of concentrated conditioned media from COS cells transfected with pSVB stop, pSV monoB or the mock transfectants.

Cells were washed once with PBS and lysed in solubilization buffer containing 20 mM Hepes, pH 7.4, 100 mM NaCl, 0.5% Nonidet P40, 10% glycerol, 1 mM PMSF and 1% aprotinin for 20 minutes at 4° C., followed by centrifugal clearance (10,000 g, 30 minutes). Crosslinking was performed with 1 mM BS$^3$ for 30 minutes at room temperature. Reaction was halted by incubation in 50 mM Tris.HCl, pH 7.5, for 10 minutes at room temperature. Immunoprecipitation and analysis was as above. Both PDGF mono B and PDGF-BB caused dimerization, as can be seen in FIG. 10B.

Example 16

Experiments were carried out to determine the arrangement of the interchain disulfide bonds between the second and fourth cysteines. To do this two new mutants were constructed, i.e., PDGF A Ser 2 with the second residue mutated to a serine residue and PDGF A Ser 4 with the fourth residue mutated to a serine residue. COS cells were transfected with pSVA(A), pSVA Ser 2, pSVA Ser 4, or both of pSVA Ser 2 and pSVA Ser 4. If interchain binding occurs between corresponding cysteine residues (e.g., 2nd cysteine to 2nd cysteine, or 4th cysteine to 4th cysteine), then cells transfected with pSVA Ser 2 or pSVA Ser 4 alone will not form dimers. Indeed, dimerization should only occur in a co-transfectant.

Cells were labelled with [$^{35}$S] cysteine, conditioned medium or medium from mock-transfected COS cells was immunoprecipitated using anti-PDGF AA antiserum, and precipitates were analyzed via SDS-gel electrophoresis, with or without DTT, followed by fluorography.

FIG. 11A shows that dimers were only found in the absence of DTT in the cotransfectants, showing that cross linkage was occurring. From this it can be concluded that the 2nd and 4th cysteine residues are disulphide bonded in crosswise fashion in the PDGF dimer.

Example 17

Tests were carried out to determine the activities of the transfectants described supra. Conditioned medium from the pSVA, pSVA Ser 2, pSVA Ser 4, and pSVA Ser 2 and pSVA Ser 4 transfectants were concentrated, desalted, and then combined with $^{125}$I-PDGF-AA to test for binding to the α receptor. FIG. 11B shows that there was competition only in the presence of the co-transfectant. These experiments also demonstrate that PDGF dimers with a single interchain band are functionally active.

Example 18

A PDGF mutant was created which does not bind to the PDGF receptor, but which is sufficiently similar to wild type PDGF to undergo normal processing and dimerization. The mutant, referred to as PDGF-O, was prepared as follows. The vector pSV7d-PDGF-A, which codes for the short splice version of PDGF-A chain and is alluded to in example 12, supra (Betsholz et al., Nature 320: 695–699 (1986); see also Östman et al., J. Biol. Chem. 2631: 16202–16208 (1988)) was used. A 1.3 kilobase cDNA which codes for the short splice variant of PDGF-A was cloned into well known vector M13. Thereafter, mutagenesis was carried out in accordance with Kunkel et al., Meth. Enzymol. 154:367–382 (1987), to substitute amino acids 156–162 by the corresponding amino acids of endothelial cell mitogen VEGF/VPG, as described by Keck et al., Science 246: 1309–1312

(1989); Leung et al., Science 246: 1306–1309 (1989). The mutated DNA was then cloned into the vector pSV7d, as described by Truett et al., DNA 4: 333–349 (1985), and referred to in the prior examples. The resulting construct, referred to hereafter as pSV7d-PDGF-O, was subjected to routine DNA sequence analysis to verify that the sequence was correct. To summarize, the resulting construct pSV7d-PDGF-O coded for a short splice variant of PDGF-A wherein amino acids 156–162, i.e., Glu Tyr Arq Lys Lys Pro (SEQ ID NO: 8)

were replaced by

Lys Pro His Gln Gly Gln His (SEQ ID NO: 9).

This choice was based upon several factors. First, the substituted sequence overlaps somewhat with one of two regions of the PDGF-B chain shown to bind to the PDGF-B receptor (Östman et al., J. Biol. Chem. 266: 10073–10077 (1991). Second, the region is hydrophilic, which suggests surface exposure on the molecule. Finally, it has been observed previously that there is perfect conservation of cysteine residues between PDGF and VEGF/VPF, suggesting that the substituted sequences would not be expected to interfere with the overall protein structure.

Example 19

Following preparation of the vector described in Example 18, supra, the construct was used to transfect eukaryotic cells. The cell line COS-1, available from the American Type Culture Collection as ATCC (CRL 1650), was cultured in Dulbecco's minimum essential medium, supplemented witch 10% fetal calf serum and antibiotics. The cells were transfected using the calcium phosphate method of Östman et al., Cell Regul 2: 503–512 (1991), using 10 ug samples of the construct, and $0.5-1 \times 10^6$ cells per 60 mm dish. Parallel cultures were also set up, using pSV7d-PDGF-A. All cultures were metabolically labelled via addition of [$^{35}$S] cysteine to the medium, for 4 hours.

Following culture, conditioned medium was removed, and the cells were lysed. Both the media and the lysates were subjected to immunoprecipitation experiments. These experiments used a polyclonal antiserum previously shown to recognize all PDGF-A isoforms (Heldin et al., Exp. Cell Res. 136: 255–261 (1981)). The immunoprecipitation took place overnight at 4° C. Protein A Sepharose CL-4B was used to collect the immunoprecipitates. These beads were incubated with the precipitate containing material for 45 minutes, after which they were washed four times with buffer (1% Triton X-100, 20 mM Tris-HCl, pH 7.5, 0.5 m NaCl, 5 mg/ml BSA, 0.1% SDS), and one time with 20 mM Tris.HCl, pH 7.5. The immune complexes were then eluted by heating the beads at 95° C. for 4 minutes in buffer (4% SDS, 0.2M Tris.HCl, pH 8.8, 0.5M sucrose, 5 mM EDTA, 0.01% bromophenol blue). Some of the samples were also subjected to reduction treatment, using 10 mM dithiothristol for two minutes at 95° C., followed by alkylation with 50 mM iodoacetamide.

Whether subjected to reducing or non-reducing conditions, all samples were then treated with SDS-gel electrophoresis in gels containing 14% polyacrylamide. Gels were soaked in "Amplify", and then exposed to Hyperfilm MP.

The results, presented in FIG. 13, show that pSV7d-PDGF-O produces a molecule which is processed to a secreted dimer having a molecular weight of about 30 kDa. This molecule, referred to hereafter as PDGF-OO (dimer) is similar in size to PDGF-AA. The monomer will be referred to hereafter as PDGF-O.

Example 20

Studies were carried out to determine the binding properties of the PDGF-OO homodimer. To do this, the conditioned media from the transfected cells (pSV7d-PDGF-O; pSV7d-PDGF-A), and mock transformed cells, were analyzed to determine if the secreted products competed with $^{125}$I-PDGF-AA for binding to the PDGF-A receptor. The experiments used cell line AG1518, a human foreskin fibroblast line, passage 10–25 (obtained from the Human Genetic Mutant Cell Repository, Camden, N.J.). The cells were grown in 24 well plates, then rinsed one time in 0.5 ml binding buffer (PBS with 1 mg/ml BSA, 0.9 mM $CaCl_2$ and 0.5 mM $MgCl_2$), then incubated for two hours at 0° C. with $^{125}$I-labelled PDGF-AA (2 ng/ml, 47,000 cpm/mg), together with one of unlabelled PDGF-AA (0–16 ng/ml), 24 hour conditioned medium from (a) mock transfectants, (b) pSV7d-PDGF-A transfectants, or (c) pSV7d-PDGF-O transfectants. Cultures were washed four times in ice cold binding buffer. The cell associated $^{125}$I radioactivity was extracted by incubation for 30 minutes at room temperature in 0.2 ml of 1% Triton X-100, 20 mM Tris.HCl, pH 7.5, and 10% (v/v) glycerol. The radioactivity was determined using a standard gamma-counter.

FIG. 14 sets forth the results. The media from the pSV7d-PDGF-A transfectants contained about 150 ng/ml of PDGF-AA activity whereas no significant activity could be detected in the pSV7d-PDGF-O transfectant medium. This experiment demonstrates that the substitution of amino acids 156–162 of the PDGF-A chain with the corresponding sequences of VEGF/VPP leads to the loss of binding to the PDGF α receptor.

Example 21

Prior work by Beckmann et al., Science 241: 1346–1349 (1988), and Fleming et al., Proc. Natl. Acad. Sci. USA 86: 8063–8067 (1989), had shown that expression of human PDGF-B in NIH 3T3 cells lead to cell transformation by autocrine activation of endogenous PDGF receptors. Investigations were thus carried out to determine if, by expression of PDGF-O chain, transformed phenotypes could be reversed via formation of a PDGF-OB heterodimer which would bind to the receptor but should not allow receptor dimerization.

To test this, NIH 3T3 cells which express PDGF-B chains (referred to hereafter as "sis3T3"), were used. The cells were cotransfected with the pSV7d-PDGF-O construct described supra, and pSV2pac, a marker for puromycin resistance. The cells were transfected using the electroporation method of Westermark et al., Proc. Natl. Acad. Sci. USA 87: 128–132 (1990), using 40 ug of pSV7d-PDGF-O and 1 ug of pSV2pac. Cells were selected 48 hours later by including 0.8 ug/ml of puromycin in the culture medium. The resistant clones were cultivated in medium supplemented with 0.5 ug/ml puromycin, and 400 ug/ml of geniticin.

Approximately 20 resistant clones were then analyzed for PDGF-O production, using the immunoprecipitation method described supra.

As FIG. 15 shows, components of 40 and 24 kDa were detected in control cell lysates, and nothing was found in the media. About half of the puromycin resistant clones had new PDGF components, of about 30 kDa, in both lysate and medium. This does not conform to any known PDGF-BB homodimer. Studies discussed infra established it to be heterodimer PDGF-OB.

Example 22

In view of the results reported in Example 21, immunoprecipitation studies were carried out using PDGF-isoform specific antiserum. Such materials are described in, e.g., Thyberg et al., J. Cell Sci. 97: 219–229 (1990). In addition, antiserum against a peptide corresponding to amino acids 156–169 of PDGF-A (Hamacher et al., J. biol. Chem. 263: 16493–16498 (1988)), was used.

The protocol for immunoprecipitation was exactly the same as that presented supra, with the exception that, prior to use of the peptide specific antiserum, cell culture medium of the sis3T3 cells was treated with 10 mM dithiothreitol (DTT) for two hours at 37° C., followed by 50 mM iodoacetamide for 0.5 hours, at neutral pH and room temperature.

These results are given in FIG. 16.

When reducing conditions were used on three cell lines producing the 30 kDa material (so-called "C15", "C111" and "C118"), the anti-AA and anti-BB antiserum gave similar results. The precipitated material was the same size as materials precipitated by anti-AA from conditioned medium of a cell line which produces only PDGF-A, i.e., cell line A172, as well as the materials precipitated from sis3T3 using anti-BB antiserum. The recognition by the two antisera suggest that the 30 kDa material is a PDGF-OB heterodimer.

These experiments did not eliminate the possibility that a PDGF-AB heterodimer was formed, hence work with an antiserum against peptide 156–169 was carried out. In results not depicted in the figures, the antiserum was found to bind the PDGF-A chain, but not PDGF-O produced by transfected COS cells. When the antiserum was tested against A172, components of 16, 17 and 23 kDa were found., i.e., three forms of PDGF-A. No such forms were detected in the media from clones 5, 11 and 18.

The conclusion to be drawn form this work is that the 16, 17 and 23 kDa components which both anti-AA and anti-BB antiserum identify in the transfected sis3T3 cells are products of PDGF-O cDNA, and that these products are part of a pDGF-OB heterodimer in these transfectants.

Example 23

Once it had been established that the sis3T3 cells were producing PDGF-O and that the mutant was associating with PDGF-B to yield a PDGF-OB heterodimer, investigations were carried out to determine if the mutant affected the known, transformed phenotype of sis3T3 cells.

Three clones from the transfections described supra which did not produce PDGF-O ("Cl.1", "Cl.6", and "Cl.19" hereafter), and three which did produce the molecule (the Cl.5, Cl.11 and Cl.18 described supra), were compared. The comparison involved three parameters: cell morphology, growth rate, and colony formation in soft agar.

With respect to the first parameter, FIG. 17 compares the clones. The non producers (Cl.1, 6, 19) were spindle shaped and exhibited criss cross growth patterns, both of which are typical of transformed cells. In contrast, Cl.5, 11 and 18 had a well organized pattern of monolayer growth.

To assess the clones' growth rates, cells were cultured in Dulbecco's minimal essential medium (DMEM) augmented with 10% fetal calf serum over a 14 day period. Medium was changed at day 7. A graph of these experiments is shown in FIG. 18, representing mean values of duplicate experiments. The PDGF-O producers were growth arrested at day 7, and by day 14 showed a five fold decrease in number as compared to PDGF-O producing cells. There were no significant differences between the 3 clones within each group.

Colony formation in soft agar was studied by plating $5 \times 10^4$ cells/mg in 12 well dishes in 0.5 ml DMEM, supplemented with 10% FCS and 0.3% low gelling temperature agarose, either with or without 50 ng/ml PDGF-BB on top of a 0.5 ml layer of the same medium, with 0.6% low temperature agarose. The dishes were monitored for three weeks, after which they were microphotographed, and the cells were counted.

The cell count is presented below in Table 5. In addition, FIG. 19 shows the microphotograph mentioned supra. The PDGF-O negative clones formed anywhere from 87 to 124 colonies per 50,000 cells, while no colonies were found in the positive clones. When PDGF-BB was added, the PDGF-O producing cells did produce colonies at the same level as the negative cells, but the colonies were smaller. One concludes, therefore, that the PDGF-O expression blocked the ability of the sis producing cells to form colonies in soft agar. The formation of colonies in the presence of PDGF-BB clearly demonstrates that lack of colony formation is not due to a general loss of responsiveness to PDGF stimulation.

TABLE 5

| Colony formation in soft agar of PDGF-0 positive and negative sis3T3 clones | | | | | |
|---|---|---|---|---|---|
| PDGF-0 positive clones | | | PDGF-0 negative clones | | |
| 5 | 11 | 18 | 1 | 6 | 19 |
| vehicle | 0 | 1 | 0 | 98 | 87 | 124 |
| PDGF-BB (50 ng/ml) | 104 | 85 | 76 | N.D. | 91 | N.D. |

The numbers represent colonies per $5 \times 10^4$ cells and are averages of triplicate determinations, 1 S.D. < 0.14. N.D., not determined.

The experiments presented supra show that various peptides and modified peptides derived from PDGF chains act as antagonists and agonists to the PDGF molecule. Preferred antagonistic peptides contain epitopes from two regions of the PDGF-B chain. The resulting peptides have amino acid sequences which, however, are not found in either wild type PDGF monomer. A preferred family of such peptides can be represented by the formula

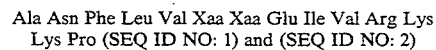
Ala Asn Phe Leu Val Xaa Xaa Glu Ile Val Arg Lys Lys Pro (SEQ ID NO: 1) and (SEQ ID NO: 2)

where the first Xaa is tryptophan or modified tryptophan, and the second Xaa comprises from 0 to 35 amino acids. Included are the peptides of SEQ ID NO: 5 and SEQ ID NO: 6. Especially preferred antagonists are the peptides referred to herein as "16" and "16T", having the amino acid sequence:

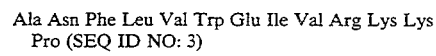
Ala Asn Phe Leu Val Trp Glu Ile Val Arg Lys Lys Pro (SEQ ID NO: 3)

and

Ala Asn Phe Leu Val Xaa Glu Ile Val Arg Lys Lys Pro (SEQ ID NO: 4)

respectively, where Xaa stands for thioanisolated tryptophan. Peptide 16T is far more efficient in competing with PDGF for receptor binding. The variant 16 NPS, in which tryptophan is coupled to 2-nitrophenylsulfenyl, is also more active as an antagonist than peptide 16. There is no immediate explanation for why these derivatives are superior to the original peptide 16, which is also active. The 13 amino acid sequence presented supra appears to be key to inhibitory/antagonistic activity. Further deletion of C-terminal amino acids, as indicated supra, resulted in insolubilization of the peptide, and thus could not be evaluated. Truncation at the N-terminal end led to loss in activity.

Previous studies have shown that amino acids 105–144 of the B chain of PDGF are important for interacting with the B receptor (LaRochelle et al., Science 248: 1541–1544 (1990)). Additional studies have led to identification of Asn-115, Arg-154 and Ile-158 as important in binding (Östman et al., J. Biol. Chem. 266: 10073–10077 (1991)). The particularly preferred peptide 16 contains amino acids 115–120 and 156–162 of PDGF-B, and thus contains some amino acids close to those identified by Östman et al. as being important; however, it must be noted that the derivatives of the invention inhibit binding to both the α and β receptors, a property not recognized by the prior work in this field. Also, the evidence presented herein shows that even minor modifications in peptide structure have profound effect on antagonistic activity. The antagonistic effect of such peptides suggests their use in conditions characterized by excess or undesirable PDGF activity. These conditions include those discussed in the "Background" section, supra, as well as chronic inflammatory conditions.

In connection with the observation on PDGF-B, it must be noted that other molecules, including vascular endothelial growth factor (vascular permeability factor or VEGF; see Keck et al., Science 246: 1309–1312 (1989); Leung et al., Science 246: 1306–1309 (1989)), and placental growth factor (Maglione et al., PNAS 88: 9267–9271 (1991)), show cysteine structures paralleling that of PDGF-B. The observations made herein suggest correlation to these other molecules, given the structural similarities.

While PDGF-A monomers were not nearly as active as the modified PDGF-B monomers, partially reduced, alkylated PDGF-A monomers did show some activity.

The examples set forth supra show, inter alia, that there is a specific pattern of cross-molecular binding which is involved in the formation of PDGF dimers. This observation can be exploited together with the observations regarding the ability to form antagonistic dimeric molecules. For example, one can control production of heterodimeric PDGF-AB, where one of the chains has been modified to produce an antagonist. The recognition of a cross bond in the dimer enables one to produce forms of PDGF-AB exclusively, subject to the single restriction that the dimer only contains a single intermolecular bond. Co-transfection of a cell with a nucleic acid molecules coding for one monomer lacking cysteine at one of the second or fourth wild type positions, and a second molecule lacking the cysteine at the other listed wild type cystine position guarantees high production of PDGF-AB. For example, if the first sequence codes for PDGF A without cysteine at the second position, and PDGF B without cysteine at fourth position, a dimer of PDGF-AB will still form, because the fourth cysteine of PDGF A can still bind the second position of PDGF B. On the other hand, dimeric PDGF AA will not form, because although the requisite fourth cysteine is present, the second cysteine is eliminated. Similar considerations dictate the absence of PDGF BB from such a system. One may, of course, produce homodimeric forms by cotransfection with nucleic acid sequences lacking the second cysteine and the fourth cysteine, but otherwise not modified. One may also transfect two separate cell samples, each with a different nucleic acid sequence, so that dimerization may occur, e.g., in the culture medium. Thus, one aspect of the invention is a kit for production of the dimers described supra, with separate nucleic acid portions coding for the desired monomer.

The invention thus encompasses antagonistic dimers produced in accordance with the principles herein, i.e., having only a single intermolecular disulfide bond. The amino acid positions described for the cysteine residues merely need modification, either by substitution by another amino acid, deletion, blocking, and so for forth. It has been shown that such a PDGF AA molecule competes for binding. Antagonists could be designed from these molecules in which one of the chains is further modified to prevent binding to the receptor such as at positions 156–162, e.g. This could then be directed to form a specific heterodimer with a wild type chain by virtue of modifying cysteine 2 or cysteine 4 in either molecule.

The foregoing disclosure also teaches the development of various amino acid containing molecules which function as antagonists to PDGF. Some of these molecules antagonize PDGF-A, and others PDGF-B. The antagonists may be monomer, or dimers. Of specific interest are those dimers which are joined by only a single cysteine bond, and molecules where the region defined by amino acids 156–162 of either PDGF-A or PDGF-B has been modified in some way. "Modified" as used herein is intended in its broadest sense, including total or partial deletion, and partial or total substitution by other amino acids. In connection with substitution by other sequence, the sequence represented by SEQ ID NO: 9 is especially preferred. It must be noted, however, that the art is well aware of conservative substitutions for amino acids, and replacement of any or all of these amino acids by conservative substitution is embraced herein.

Those antagonists which contain the aforementioned modifications may be used in the form of monomers or dimers, the dimeric molecule referred to herein as "PDGF-OB" being especially preferred. It must be noted, however, that the art is well aware of conservative substitutions for amino acids, and replacement of any or all of these amino acids by conservative substitution is embraced herein.

Those antagonists which contain the aforementioned modifications may be used in the form of monomers or dimers, the dimeric molecule referred to herein as "PDGF-OB" being especially preferred. All such dimeric, PDGF antagonists are characterized by being able to bind to PDGF receptors and by inhibiting dimerization of these receptors. Receptor dimerization is necessary for PDGF activity, hence the antagonistic effect. The antagonists described herein may be made, e.g., via expression of the nucleic acid sequences which code for them. These sequences may be incorporated into expression vectors, such as plasmids, whereby the coding sequences are operably linked to promoters. The expression vectors, as well as the nucleic acid sequences themselves, may serve as transfecting agents so as to produce cell lines which manufacture the antagonists. Eukaryotic cells, such as COS cells, are preferred.

It has been pointed out, supra, that the antagonists of the invention may be used in dimeric form. It is particularly preferred that when dimers are used, that one monomer be a normal PDGF monomer, and the other be modified. Such dimers can be produced recombinantly, by using host cells which produce one normal PDGF molecule and one modified molecule. One may produce the dimers via, e.g., cotransfection with appropriate nucleic acids, or via transfection of a cell which produces one normal PDGF molecule with nucleic acids coding for the second, modified molecule. Either PDGF-A or PDGF-B may serve as the normal monomer, and also as the modified monomer. One aspect of the invention is the provision of kits for enabling the artisan to make such dimers. In their broadest aspect, such kits include nucleic acid sequences for both PDGF monomers, preferably in the form of expression vectors. Such kits may also include additional reagents useful in transfection of cells, such as are known to the skilled artisan.

In addition to the other uses to which the antagonists of the invention may be put, as have been alluded to supra, the examples show that PDGF-B linked cell transformation may be relieved and reversed via administration of antagonists to PDGF-B. Thus, one aspect of the invention is a method for inhibiting an adverse effect of PDGF-B in a subject by administering a PDGF-B antagonist to the subject in an amount sufficient to inhibit the PDGF-B's effect. Cell transformation is one such adverse effect. Others are known to the artisan, such as those adumbrated in this application. Other aspects of the invention will be clear to the skilled artisan and do not require elaboration herein.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

---

We claim:

1. Isolated peptide antagonist for platelet derived growth factor, consisting of amino acid sequence:

Ala Asn Phe Leu Val Xaa Xaa Glu Ile Val Arg Lys
    Lys Pro (SEQ ID NO: 2)

wherein the first Xaa is modified tryptophan, and the second Xaa is anywhere from 0 to 35 amino acids.

2. The isolated peptide antagonist of claim 1, wherein the second Xaa is 0 amino acids.

3. The isolated peptide antagonist of claim 2, wherein the first Xaa is thioanisolated tryptophan, or a 2-nitrophenyl sulfenyl chloride derivative of tryptophan.

4. The isolated peptide antagonist of claim 1, wherein the second Xaa is Pro Pro Cys Val Glu Val Gln Leu Arg Pro Val Gln Val Arg Lys Ile, which corresponds to amino acids 7–22 of SEQ ID NO: 5.

5. The isolated peptide antagonist of claim 4, wherein the first Xaa is thioanisolated tryptophan or a 2-nitrophenylsulfenyl tryptophan derivative.

\* \* \* \* \*

SEQUENCE LISTING ( 1 ) GENERAL INFORMATION:

( i i i ) NUMBER OF SEQUENCES: 10

( 2 ) INFORMATION FOR SEQ ID NO: 1:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( D ) OTHER INFORMATION: Xaa is anywhere from 0 to 35 amino acids ( x i ) SEQUENCE DESCRIPTION: SEQ ID NO: 1:

Ala  Asn  Phe  Leu  Val  Trp  Xaa  Glu  Ile  Val  Arg  Lys  Lys  Pro
        5                                10

( 2 ) INFORMATION FOR SEQ ID NO: 2:

( i ) SEQUENCE CHARACTERISTICS:
        ( A ) LENGTH: 14 amino acids
        ( B ) TYPE: amino acid
        ( D ) TOPOLOGY: linear ( i i ) MOLECULE TYPE: protein ( i x ) FEATURE:
        ( D ) OTHER INFORMATION: the first Xaa is tryptophan or
        modified tryptophan; the second Xaa stands
        for anywhere from 0 to 35 amino acids ( x i ) SEQUENCE DESCRIPTION: SEQ ID NO: 2:

Ala  Asn  Phe  Leu  Val  Xaa  Xaa  Glu  Ile  Val  Arg  Lys  Lys  Pro
        5                              10

( 2 ) INFORMATION FOR SEQ ID NO: 3:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 3:

Ala Asn Phe Leu Val Trp Glu Ile Val Arg Lys Lys Pro
            5                10

( 2 ) INFORMATION FOR SEQ ID NO: 4:

( i ) SEQUENCE CHARACTERISTICS:
    ( A ) LENGTH: 13 amino acids
    ( B ) TYPE: amino acid
    ( D ) TOPOLOGY: linear ( i i ) MOLECULE TYPE: protein ( i x ) FEATURE:
    ( D ) OTHER INFORMATION: Xaa is tryptophan or thioanisolated
      tryptophan ( x i ) SEQUENCE DESCRIPTION: SEQ ID NO: 4:

Ala Asn Phe Leu Val Xaa Glu Ile Val Arg Lys Lys Pro
            5               10

( 2 ) INFORMATION FOR SEQ ID NO: 5:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: protein ( i x ) FEATURE:
    ( D ) OTHER INFORMATION: Xaa is tryptophan or a modified
      tryptophan, such as thioanisolated
      tryptophan or a 2-nitrophenyl sulfenyl
      derivative of tryptophan ( x i ) SEQUENCE DESCRIPTION: SEQ ID NO: 5:

Ala Asn Phe Leu Val Xaa Pro Pro Cys Val Glu Val Gln Leu Arg Pro
            5          10         15

Val Gln Val Arg Lys Ile Glu Ile Val Arg Lys Lys Pro
            20          25

( 2 ) INFORMATION FOR SEQ ID NO: 6:

( i ) SEQUENCE CHARACTERISTICS:
    ( A ) LENGTH: 29 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 6:

Ala Asn Phe Leu Val Trp Pro Pro Cys Val Glu Val Gln Leu Arg Pro
            5          10         15

Val Gln Val Arg Lys Ile Glu Ile Val Arg Lys Lys Pro
            20          25

( 2 ) INFORMATION FOR SEQ ID NO: 7:

( i ) SEQUENCE CHARACTERISTICS:
    ( A ) LENGTH: 125 amino acids
    ( B ) TYPE: amino acid
    ( D ) TOPOLOGY: linear ( i i ) MOLECULE TYPE: protein ( x i ) SEQUENCE DESCRIPTION: SEQ ID NO: 7:

Ser Ile Glu Glu Ala Val Pro Ala Val Cys Lys Thr Arg Thr Val Ile
            5          10         15

Tyr Glu Ile Pro Arg Ser Gln Val Asp Pro Thr Ser Ala Asn Phe Leu
            20          25         30

Ile Trp Pro Pro Cys Val Glu Val Lys Arg Cys Thr Gly Cys Cys Asn

```
                       3 5                         4 0                              4 5
         Thr Ser Ser Val Lys Cys Gln Pro Ser Arg Val His His Arg Ser Val
             5 0                          5 5                 6 0
         Lys Val Ala Lys Val Glu Tyr Val Arg Lys Lys Pro Lys Leu Lys Glu
         6 5                     7 0                  7 5                         8 0
         Val Gln Val Arg Leu Glu Glu His Leu Glu Cys Ala Cys Ala Thr Thr
                         8 5                  9 0                          9 5
         Ser Leu Asn Pro Asp Tyr Arg Glu Glu Asp Thr Gly Arg Pro Arg Glu
                     1 0 0                     1 0 5                 1 1 0
         Ser Gly Lys Lys Arg Lys Arg Lys Arg Leu Lys Pro Thr
                     1 1 5             1 2 0                 1 2 5
```

( 2 ) INFORMATION FOR SEQ ID NO: 8:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 8:

```
         Glu Tyr Val Arg Lys Lys Pro
                         5
```

( 2 ) INFORMATION FOR SEQ ID NO: 9:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 9:

```
         Lys Pro His Gln Gly Gln His
                         5
```

( 2 ) INFORMATION FOR SEQ ID NO: 10:

( i ) SEQUENCE CHARACTERISTICS:
        ( A ) LENGTH: 13 amino acids
        ( B ) TYPE: amino acid
        ( D ) TOPOLOGY: linear ( i i ) MOLECULE TYPE: protein ( i v ) FEATURE:
        ( D ) OTHER INFORMATION: Xaa is tryptophan or tryptophan modified
            by thioanisole ( x i ) SEQUENCE DESCRIPTION: SEQ ID NO: 10:

```
         Glu Ala Phe Ile Lys Xaa Leu Val Arg Asn Lys Val Pro
                         5                         1 0
```